United States Patent
Rozenblum et al.

(10) Patent No.: US 11,376,302 B2
(45) Date of Patent: Jul. 5, 2022

(54) METHODS FOR TREATING DEPRESSION AND MAJOR DEPRESSIVE DISORDER

(71) Applicant: CARMEL HAIFA UNIVERSITY ECONOMIC CORPORATION LTD., Haifa (IL)

(72) Inventors: Yaacov Rozenblum, Zikhron Ya'akov (IL); Elham Taha, Kabul (IL); Chinnakkaruppan Adaikkan, Somerville, MA (US)

(73) Assignee: CARMEL HAIFA UNIVERSITY ECONOMIC CORPORATION LTD., Haifa (IL)

( * ) Notice: Subject to any disclaimer, the term of this patent is extended or adjusted under 35 U.S.C. 154(b) by 0 days.

(21) Appl. No.: 16/645,581

(22) PCT Filed: Sep. 6, 2018

(86) PCT No.: PCT/IL2018/051010
§ 371 (c)(1),
(2) Date: Mar. 9, 2020

(87) PCT Pub. No.: WO2019/049148
PCT Pub. Date: Mar. 14, 2019

(65) Prior Publication Data
US 2020/0215147 A1 Jul. 9, 2020

Related U.S. Application Data

(60) Provisional application No. 62/556,440, filed on Sep. 10, 2017.

(51) Int. Cl.
| | |
|---|---|
| *A61P 25/24* | (2006.01) |
| *A61K 38/00* | (2006.01) |
| *A61K 31/135* | (2006.01) |
| *A61K 38/16* | (2006.01) |

(52) U.S. Cl.
CPC .......... *A61K 38/005* (2013.01); *A61K 31/135* (2013.01); *A61K 38/162* (2013.01); *A61P 25/24* (2018.01)

(58) Field of Classification Search
CPC .. A61K 38/005; A61K 31/135; A61K 38/162; A61K 38/00; A61P 25/24; G01N 2500/00; G01N 2800/304; G01N 33/6896; G01N 2333/4727
See application file for complete search history.

(56) References Cited

U.S. PATENT DOCUMENTS

| | | |
|---|---|---|
| 2010/0304391 A1 | 12/2010 | Lombard |
| 2017/0247374 A1 | 8/2017 | Levy et al. |

FOREIGN PATENT DOCUMENTS

| | | |
|---|---|---|
| WO | 2009042906 A1 | 4/2009 |
| WO | 2015018375 A1 | 2/2015 |

OTHER PUBLICATIONS

Coultrap et al (Cell Reports, 2014, 6, 431-437) (Year: 2014).*
Vest et al (Molecular Biology of the Cell, 2007, 18, 5024-5033). (Year: 2007).*
Coultrap et al. "Autonomous CaMKII mediates both LTP and LTD using a mechanism for differential substrate site selection." Cell reports 6.3 (2014): 431-437.
Robison et al. "Fluoxetine epigenetically alters the CaMKII? promoter in nucleus accumbens to regulate ?FosB binding and antidepressant effects." Neuropsychopharmacology39.5 (2014): 1178.
Xu et al. "Effects of low-dose and very low-dose ketamine among patients with major depression: a systematic review and meta-analysis." International Journal of Neuropsychopharmacology 19.4 (2016).
Rasmussen et al. "Serial infusions of low-dose ketamine for major depression." Journal of Psychopharmacology 27.5 (2013): 444-450.
Liu et al. "GSK-3 inhibition potentiates the synaptogenic and antidepressant-like effects of subthreshold doses of ketamine." Neuropsychopharmacology 38.11 (2013): 2268.
Yang et al. "Acute administration of ketamine in rats increases hippocampal BDNF and mTOR levels during forced swimming test." Upsala journal of medical sciences 118.1 (2013): 3-8.
Vigil et al., "Prevention of long-term memory loss after retrieval by an endogenous CaMKII inhibitor", Scientific Reports, Scientific Reports, 7(1), 4040, 2017.
Wang et al., "The emerging role of CaMKII in cancer", Oncotarget, vol. 6, No. 14, pp. 11725-11734, 2015.
Coultrap et al., "Improving a Natural CaMKII Inhibitor by Random and Rational Design" PLoS ONE, 6(10), e25245. 2011.
International Search Report for PCT/IL2018/051010 Completed Dec. 26, 2018; dated Dec. 26, 2018 4 pages.
Written Opinion for PCT/IL2018/051010 Completed Dec. 26, 2018; dated Dec. 26, 2018 10 pages.
Li, K. et al., (2013). CaMKII in Lateral Habenula Mediates Core Symptoms of Depression. Science, 341(6149), 1016-1020.
Ahmed, M. et al., (2016). Beneficial Effects of a CaMKIIα Inhibitor TatCN21 Peptide in Global Cerebral Ischemia. Journal of Molecular Neuroscience, 61(1), 42-51.

* cited by examiner

*Primary Examiner* — Sudhakar Katakam

(74) *Attorney, Agent, or Firm* — The Roy Gross Law Firm, LLC; Roy Gross

(57) ABSTRACT

Methods for treating depression in, and decreasing a dose of ketamine given to, a subject in need thereof, comprising, administering a CaMKII inhibitor are provided.

15 Claims, 21 Drawing Sheets

Specification includes a Sequence Listing.

METHODS FOR TREATING DEPRESSION AND MAJOR DEPRESSIVE DISORDER

CROSS REFERENCE TO RELATED APPLICATIONS

This application is a National Phase of PCT Patent Application No. PCT/IL2018/051010 having International filing date of Sep. 6, 2018, which claims the benefit of priority of U.S. Provisional Patent Application No. 62/556,440, filed Sep. 10, 2017, the contents of the above applications are all incorporated by reference as if fully set forth herein in their entirety.

FIELD OF INVENTION

The present invention is directed to methods of treating depression with a CaMKII inhibitor.

BACKGROUND OF THE INVENTION

Major depressive disorder (MDD) is characterized by persistent lack of interest in physical and mental activities, and causes detrimental changes in normal life, thereby creating a burden on the family and society. Clinical studies have shown that classical anti-depressant drugs that reduce depression are effective in relatively less percentage of MDD patients. These drugs also take days to weeks to elicit the antidepressant effect. Remarkably, however, a single intravenous administration of ketamine, an antagonist of ionotropic glutamatergic N-methyl-D-aspartate receptor (NMDAR), is sufficient to reduce depression in human patients and its effect also persists for many hours to days.

Intensive investigations trying to understand the cellular and molecular mechanisms of ketamine action has brought several key insights: ketamine administration leads to rapid synthesis of proteins such as brain-derived neurotrophic factor (BDNF) and GluA1 subunit of α-amino-3-hydroxy-5-methyl-4-isoxazolepropionic acid receptor (AMPAR). Up-regulated BDNF together with other dendritic/synaptic proteins such as GluA1 trigger evoked synaptic transmission to mediate the long-lasting effects of ketamine. Ketamine-mediated new synthesis of BDNF requires the deactivation of eEF2K (also known as calcium/calmodulin dependent kinase III; a translation regulation kinase involved in the elongation phase), and subsequently reduced phosphorylation of eEF2 on Thr-56. This mechanistic insight is further supported by the findings that eEF2K inhibitors induce fast behavioral antidepressant effects in mice.

Ketamine has many known side effects, and new methods for rapid and prolonged treatment of major depressive disorders are still greatly needed.

SUMMARY OF THE INVENTION

The present invention provides methods for treating depression and decreasing a dose of ketamine administered to a subject, by administering a CaMKII inhibitor. Kits for doing same are also provided.

According to a first aspect, there is provided a method for treating or ameliorating depression in a subject in need thereof, the method comprising administering to the subject a calcium/calmodulin-dependent protein kinase II (CaMKII) inhibitor.

According to another aspect, there is provided a method for reducing the dose of ketamine given to a subject in need thereof, the method comprising administering to the subject a CaMKII inhibitor.

In some embodiments, the subject in need of a dose of ketamine suffers from depression. In some embodiments, the depression is major depressive disorder.

In some embodiments, the CaMKII inhibitor inhibits calcium-stimulated substrate phosphorylation. In some embodiments, the CaMKII inhibitor inhibits autonomous substrate phosphorylation. In some embodiments, the CaMKII inhibitor increases auto-inhibitory phosphorylation of CaMKII. In some embodiments, the inhibitory phosphorylation comprises phosphorylation of threonine 305 of CAMK2A. In some embodiments, the CaMKII inhibitor decreases auto-activating phosphorylation of CaMKII. In some embodiments, the activating phosphorylation comprises phosphorylation of threonine 286 of CAMK2A. In some embodiments, the CaMKII inhibitor does not affect CaMKII protein levels.

In some embodiments, the CaMKII inhibitor is TatCN21. In some embodiments, the subject is a human and between 0.08 mg/kg body weight and 0.8 mg/kg body weight of the TatCN21 is administered. In some embodiments, between 0.08 and 0.4 mg/kg body weight is administered.

In some embodiments, the administering is any one of oral administering, intravenous administering, and intraperitoneal administering. In some embodiments, the administering is intraperitoneal administering.

In some embodiments, the administering increases global protein synthesis in a brain tissue of the subject. In some embodiments, the brain tissue is selected from hippocampus and cortex. In some embodiments, the brain tissue is hippocampus.

In some embodiments, the treating or ameliorating occurs in less than 1 hour from the administering. In some embodiments, the treating or ameliorating persists for at least 24 hours.

In some embodiments, the methods of the invention further comprising administering to the subject a CaMKII activator at least 30 minutes after administering the inhibitor.

In some embodiments, the reducing is at least a 10% reduction.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
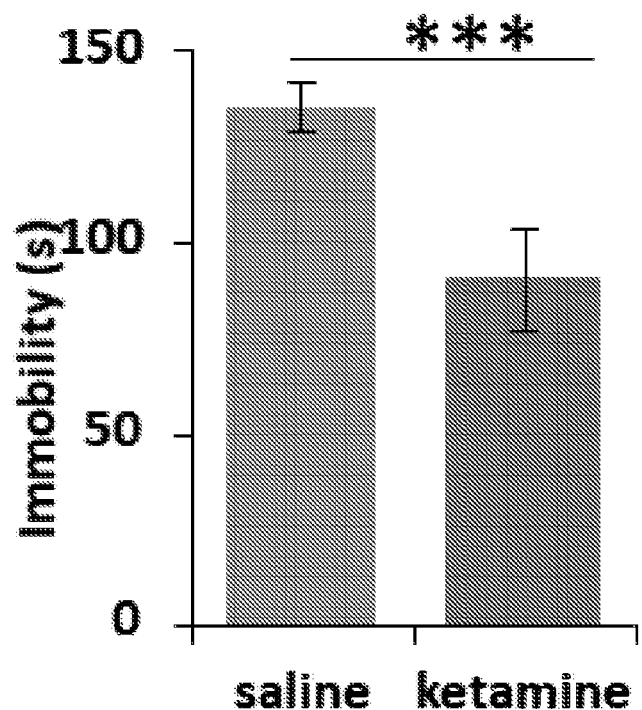
FIGS. 1A-1M. The antidepressant ketamine activates CaMKII and eEF2 signaling. (1A) Bar graph showing time of immobility of mice during forced swim test. (1B) Line graph showing pT56eEF2 expression in the hippocampus after ketamine injection. (1C) Bar chart of peIF2a and EIF2a from hippocampal (left) and cortical (right) samples. (1D) Representative immunoblot of SUnSET method of protein quantification on hippocampal tissue. (1E) Bar chart quantification of protein synthesis. (1F, 1G) Dot plots showing phosphorylation status of CaMKIIα (pT286) and CaMKIII substrate eEF2 (pT56) were positively correlated at basal levels in the (1F) hippocampus and (1G) cortex. (1H, 1I) Line graphs showing pT286 CaMKIIα was slightly increased 40 min after ketamine administration in the (1H) hippocampus and (1I) cortex. (1J, 1K) Line graphs showing inhibitory phosphorylation of CaMKIIα (pT305) was significantly increased 20 min after ketamine administration in the (1J) hippocampus and (1K) cortex. (1L, 1M) Line graphs showing there was no difference in total CaMKIIα levels in the (1L) hippocampus and (1M) cortex.

The present invention provides, in some embodiments, methods for treating depression and decreasing a dose of ketamine administered to treat depression, by administering a CaMKII inhibitor.

By a first aspect, there is provided a method for treating or ameliorating depression in a subject in need thereof, the method comprising administering to the subject a CaMKII inhibitor.

By another aspect, there is provided a method for reducing the dose of ketamine given to a subject in need thereof, the method comprising administer to the subject a CaMKII inhibitor.

By another aspect, there is provided a method for treating or ameliorating depression, or reducing the dose of ketamine given to a subject in need thereof, the method comprising
 a. transiently decreasing CaMKII kinase function in the subject; and
 b. increasing CaMKII kinase function in the subject;
thereby treating or ameliorating depression or reducing the dose of ketamine given to a subject.

As used herein, "calcium/calmodulin-dependent protein kinase II (CaMKII)" refers to a protein kinase highly expressed in the brains of mammals that is well known in the art. There are at least 4 different isoforms of CaMK2 that differ slightly in amino acid sequence: CaMK2A, CaMK2B, CaMK2D and CaMK2G. CaMKII and CaMK2 are used interchangeably herein. In some embodiments, CaMKII is CaMKIIalpha (CaMKIIa). In some embodiments, CaMKII is CaMKIIIbeta (CaMKIIb). In some embodiments, CaMKII is CaMKIIa and/or CaMKIIb. In some embodiments, CaMKII is neuronal CaMKII. In some embodiments, CaMKII is mammalian CaMKII. In some embodiments, CaMKII is rodent CaMKII. In some embodiments, CaMKII is human CaMKII.

In some embodiments, the amino acid sequence of CaMKII and/or CaMKIIa is provided in accession number NP_001350919.1, NP_001350918.1, XP_016865387.1, NP_741960.1, or NP_057065.2. Each possibility represents a separate embodiment of the invention. In some embodiments, the amino acid sequence of CaMKII and/or CaMKIIb is provided in accession number NP_001211.3, NP_742075.1, NP_742076.1, NP_742077.1, NP_743078.1, NP_742079.1, NP_742080.1 or NP_742081.1. Each possibility represents a separate embodiment of the invention. In some embodiments, CaMKII and/or CaMKIIa comprises or consists of the sequence MATITCTRFTEEYQLFEELGK-GAFSVVRRCVKVLAGQEYAAKIINTKKL-SARDHQKLER EARICRLLKHPNIVRLHDSI-SEEGHHYLIFDLVTGGELFEDIVAREYYSEADASHCI QQILE AVLHCHQMGVVHRDLKPENLLLASKLK-GAAVKLADFGLAIEVEGEQQAWFGFAGTPG YLSPE-VLRKDPYGKPVDLWACGVILYILLVGYPPFWD-EDQHRLYQQIKAGAYDFPSPEW DTVTPEAKDLINKMLTINPSKRITAAEALKHPWISH-RSTVASCMHRQETVDCLKKFNARR KLKGAILTTM-LATRNFSGGKSGGNKKSDGVKESSESTNTTIE-DEDTKVRKQEIIKVTEQLI EAISNGDFESYTKMCDPGMTAFEPEALGNLVEG-LDFHRFYFENLWSRNSKPVHTTILNPH IHLMGDESA-CIAYIRITQYLDAGGIPRTAQSEETRVWHRRDGKWQI-VHFHRSGAPSVLPH (SEQ ID NO: 2). In some embodiments, CaMKII and/or CaMKIIb comprises or consists of the sequence (SEQ ID NO: 3)
MATTVTCTRFTDEYQLYEDIGKGAFSVVRRCVKLCTGHEYAAKIINTK

KLSARDHQKLEREARICRLLKHSNIVRLHDSISEEGFHYLVFDLVTGG

ELFEDIVAREYYSEADASHCIQQILEAVLHCHQMGVVHRDLKPENLLL

-continued

ASKCKGAAVKLADFGLAIEVQGDQQAWFGFAGTPGYLSPEVLRKEAYG

KPVDIWACGVILYILLVGYPPFWDEDQHKLYQQIKAGAYDFPSPEWDT

VTPEAKNLINQMLTINPAKRITAHEALKHPWVCQRSTVASMMHRQETV

ECLKKFNARRKLKGAILTTMLATRNFSVGRQTTAPATMSTAASGTTMG

LVEQAKSLLNKKADGVKPQTNSTKNSAAATSPKGTLPPAALEPQTTVI

HNPVDGIKESSDSANTTIEDEDAKARKQEIIKTTEQLIEAVNNGDFEA

YAKICDPGLTSFEPEALGNLVEGMDFHRFYFENLLAKNSKPIHTTILN

PHVHVIGEDAACIAYIRLTQYIDGQGRPRTSQSEETRVWHRRDGKWQN

VHFHCSGAPVAPLQ.

In some embodiments, the subject is a mammal. In some embodiments, the subject is a human. In some embodiments, a subject in need of treatment with a dose of ketamine suffers from depression. As used herein, "depression" refers to a mood disorder in which a person feels sadness and/or loss of interests at a frequency above what is normal. Depression is not a neurological disorder selected from Alzheimer's disease, schizophrenia, drug addiction, epilepsy, or developmental retardation. In some embodiments, depression comprises major depressive disorder, persistent depressive disorder, perinatal depression, psychotic depression, postpartum depression, seasonal affective disorder, bipolar disorder or clinical depression. In some embodiments, depression is major depressive disorder.

Depression and its symptoms will be well known to a person of skill in the art. In some embodiments, depression comprises depressive symptoms that have persisted for at least a week, two weeks, a month, two months, half a year, a year or two years. Each possibility represents a separate embodiment of the invention. Methods of diagnosing depression include, but are not limited to questioning of the subject, a physical examination, blood work, sleep monitoring, and eating monitoring.

As used herein, the terms "administering," "administration," and like terms refer to any method which, in sound medical practice, delivers a composition containing an active agent to a subject in such a manner as to provide a therapeutic effect. One aspect of the present subject matter provides for intraperitoneal administration of a therapeutically effective amount of CamKII inhibitor to a patient in need thereof. One aspect of the present subject matter provides for oral administration of a therapeutically effective amount of CamKII inhibitor to a patient in need thereof. Other suitable routes of administration can include parenteral, subcutaneous, intravenous, intramuscular, or intranasally. In some embodiments, the administering is any one of oral, intravenous and intraperitoneal. In some embodiments, a therapeutically effective dose of the CaMKII inhibitor is administered.

In some embodiments, the CaMKII inhibitor is administered daily. In some embodiments, the inhibitor is administered weekly. In some embodiments, the inhibitor is administered as needed by the subject. In some embodiments, the inhibitor is administered in response to a depressive symptom or incident. In some embodiments, the inhibitor is administered indefinitely for the life of the subject.

In some embodiments, CaMKII is anyone of CAMK2A, CAMK2B, CAMK2D and CAMK2G. In some embodiments, CaMKII is CAMK2A. CaMKII, also known as calcium ($Ca^{2+}$)/calmodulin-dependent protein kinase II, is a multifunctional protein kinase. CaMKII phosphorylates multiple substrates in calcium-dependent, calmodulin-dependent and autonomous fashion. CaMKII is also known to perform autophosphorylation.

As used herein, a "CaMKII inhibitor" is a protein, small molecule or drug that represses the kinase function of CaMKII. In some embodiments, the CaMKII inhibitor decreases calcium-stimulated or calcium-dependent substrate phosphorylation. In some embodiments, the CaMKII inhibitor decreases CaMKII kinase function. In some embodiments, the CaMKII inhibitor decreases autonomous substrate phosphorylation. In some embodiments, the decrease is at least a 10%, 20%, 30%, 40% 50%, 60%, 70%, 80%, 90%, 95%, 97%, 99%, or 100% decrease. Each possibility represents a separate embodiment of the invention. In some embodiments, the CaMKII inhibitor increases auto-inhibitory phosphorylation of CaMKII. In some embodiments, auto-inhibitory phosphorylation comprises phosphorylation of threonine 305 of CAMK2A. In some embodiments, auto-inhibitory phosphorylation comprises phosphorylation of threonine 305 of SEQ ID NO: 2. In some embodiments, auto-inhibitory phosphorylation comprises phosphorylation of threonine 321 of CAMK2B. In some embodiments, auto-inhibitory phosphorylation comprises phosphorylation of threonine 321 of SEQ ID NO: 3. In some embodiments, inhibitory phosphorylation comprises phosphorylation of a homologous amino acid to threonine 305 of CAMK2A. In some embodiments, the increase is at least a 10%, 20%, 30%, 40%, 50%, 60%, 70%, 80%, 90%, 100%, 150%, 200%, 250%, 300%, 350%, 400%, 450%, or 500% increase. Each possibility represents a separate embodiment of the invention. In some embodiments, the inhibitor completely inhibits autonomous substrate phosphorylation and/or calcium-dependent substrate phosphorylation.

In some embodiments, the CaMKII inhibitor has no effect on auto-activating phosphorylation of CaMKII. In some embodiments, the CaMKII inhibitor partially decreases auto-activating phosphorylation of CaMKII. In some embodiments, the CaMKII inhibitor decreases auto-activating phosphorylation of CaMKII. In some embodiments, auto-activating phosphorylation comprises phosphorylation of threonine 286 of CAMK2A. In some embodiments, auto-activating phosphorylation comprises phosphorylation of threonine 286 of SEQ ID NO: 2. In some embodiments, auto-activating phosphorylation comprises phosphorylation of threonine 287 of CAMK2B. In some embodiments, auto-activating phosphorylation comprises phosphorylation of threonine 287 of SEQ ID NO: 3. In some embodiments, activating phosphorylation comprises phosphorylation of a homologous amino acid to threonine 286 of CAMK2A. In some embodiments, the decrease in auto-activating phosphorylation is at least a 10%, 20%, 30%, 40% 50%, 60%, 70%, 80%, 90%, 95%, 97%, 99%, or 100% decrease. Each possibility represents a separate embodiment of the invention.

In some embodiments, the CaMKII inhibitor does not affect CaMKII protein levels. In some embodiments, the CaMKII inhibitor does not increase CaMKII protein levels. In some embodiments, the CaMKII inhibitor does not decrease CaMKII protein levels. In some embodiments, the CaMKII inhibitor does not alter CaMKII transcription, translation or both. Each possibility represents a separate embodiment of the invention.

In some embodiments, the CaMKII inhibitor is TatCN21. In some embodiments, TatCN21 comprises a 21-amino acid peptide CN21, which is fused with the cell permeable peptide Tat. In some embodiments, TatCN21 consists of a 21-amino acid peptide CN21, which is fused with the cell permeable peptide Tat. In some embodiments, CN21 consists of the sequence KRPPKLGQIGRSKRVVIEDDR (SEQ ID NO: 1). In some embodiments, Tat consists or comprises the sequence GRKKRRQRRRPQ (SEQ ID NO: 4). TatCN21 is commercially available from retailers such as Merck or can be synthesized by routine molecular biology techniques.

The dosage administered will be dependent upon the age, health, and weight of the recipient, kind of concurrent treatment, if any, frequency of treatment, and the nature of the effect desired. In some embodiments, the dosage of CamKII inhibitor for reduction of ketamine administration is lower than the dose when the inhibitor is used alone as treatment. In some embodiments, the inhibitor is TatCN21, the subject is a rodent or mouse and between 1 mg/kg body weight and 10 mg/kg body weight are administered. In some embodiments, the inhibitor is TatCN21, the subject is a rodent or mouse and between 1 mg/kg body weight and 5 mg/kg body weight are administered. In some embodiments, between 0.1 and 20, 0.1 and 15, 0.1 and 10, 0.1 and 5, 0.25 and 20, 0.25 and 15, 0.25 and 10, 0.25 and 5, 0.5 and 20, 0.5 and 15, 0.5 and 10, 0.5 and 5, 1 and 20, 1 and 15, 1 and 10, or 1 and 5 mg/kg body weight of CaMKII inhibitor is administered. Each possibility represents a separate embodiment of the invention. In some embodiments, 1 to 5000, 1 to 4500, 1 to 4000, 1 to 3500, 1 to 3000, 1 to 2500, 1 to 2000, 1 to 1500, 1 to 1000, 1 to 900, 1 to 800, 1 to 700, 1 to 600, 1 to 500, 1 to 400, 1 to 300, 1 to 200 or 1 to 100 mg of CaMKII inhibitor is administered. Each possibility represents a separate embodiment of the invention. In some embodiments, the inhibitor is TatCN21, the subject is a human and between 0.08 mg/kg body weight and 0.8 mg/kg body weight are administered. In some embodiments, between 0.001 and 10, 0.001 and 5, 0.001 and 2.5, 0.001 and 2, 0.001 and 1.5, 0.001 and 1, 0.001 and 0.8, 0.001 and 0.6, 0.001 and 0.4, 0.001 and 0.2, 0.001 and 0.1, 0.005 and 10, 0.005 and 5, 0.005 and 2.5, 0.005 and 2, 0.005 and 1.5, 0.005 and 1, 0.005 and 0.8, 0.005 and 0.6, 0.005 and 0.4, 0.005 and 0.2, 0.005 and 0.1, 0.01 and 10, 0.01 and 5, 0.01 and 2.5, 0.01 and 2, 0.01 and 1.5, 0.01 and 1, 0.01 and 0.8, 0.01 and 0.6, 0.01 and 0.4, 0.01 and 0.2, 0.01 and 0.1, 0.05 and 10, 0.05 and 5, 0.05 and 2.5, 0.05 and 2, 0.05 and 1.5, 0.05 and 1, 0.05 and 0.8, 0.05 and 0.6, 0.05 and 0.4, 0.05 and 0.2, 0.05 and 0.1, 0.08 and 10, 0.08 and 5, 0.08 and 2.5, 0.08 and 2, 0.08 and 1.5, 0.08 and 1, 0.08 and 0.8, 0.08 and 0.6, 0.08 and 0.4, 0.08 and 0.2, 0.08 and 0.1, 0.1 and 10, 0.1 and 5, 0.1 and 2.5, 0.1 and 2, 0.1 and 1.5, 0.1 and 1, 0.1 and 0.8, 0.1 and 0.6, 0.1 and 0.4, 0.1 and 0.2, 0.2 and 10, 0.2 and 5, 0.2 and 2.5, 0.2 and 2, 0.2 and 1.5, 0.2 and 1, 0.2 and 0.8, 0.2 and 0.6, 0.2 and 0.4, 0.3 and 10, 0.3 and 5, 0.3 and 2.5, 0.3 and 2, 0.3 and 1.5, 0.3 and 1, 0.3 and 0.8, 0.3 and 0.6, 0.3 and 0.4, 0.4 and 10, 0.4 and 5, 0.4 and 2.5, 0.4 and 2, 0.4 and 1.5, 0.4 and 1, 0.4 and 0.8, 0.4 and 0.6, 0.5 and 10, 0.5 and 5, 0.5 and 2.5, 0.5 and 2, 0.5 and 1.5, 0.5 and 1, 0.5 and 0.8, or 0.5 and 0.6, mg/kg body weight of CaMKII inhibitor is administered. Each possibility represents a separate embodiment of the invention. In some embodiments, the inhibitor is TatCN21, the subject is a human and between 0.08 mg/kg body weight and 0.4 mg/kg body weight are administered.

In some embodiments, the CamKII inhibitor is administered with an adjuvant, carrier or excipient. As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

In some embodiments, the administering increases global protein synthesis in a subject. In some embodiments, the administering increases global protein synthesis in a brain tissue of the subject. In some embodiments, the brain tissue is selected from hippocampus and cortex. In some embodiments, the brain tissue is cortex. In some embodiments, the brain tissue is hippocampus. In some embodiments, the administering increases synthesis of BDNF. In some embodiments, the administering does not affect synthesis of BDNF. In some embodiments, the administering increases synthesis of GluA1. In some embodiments, the administering does not affect synthesis of GluA1.

In some embodiments, the administering does not cause side effect. In some embodiments, the side effects are ketamine-associated side effects. In some embodiments, the side effects are ketamine infusion therapy side effects. In some embodiments, the administering causes fewer side effects than ketamine administration. Side effects caused by ketamine treatment are known in the art, and include but are not limited to, psychotic symptoms, dissociative symptoms, abnormal sensations, blurred vision, drowsiness, elevated heart rate and elevated blood pressure.

In some embodiments, the treating or ameliorating occurs in less than 30 minutes, 45 minutes, 1 hour, 90 minutes, or 2 hours after the administering. Each possibility represents a separate embodiment of the invention. In some embodiments, at least one depressive symptom is decreased or alleviated in less than 30 minutes, 45 minutes, 1 hour, 90 minutes, or 2 hours after the administering. Each possibility represents a separate embodiment of the invention. In some embodiments, the treating or ameliorating occurs in less than 1 hour from the administering. In some embodiments, at least one depressive symptom is decreased or alleviated in less than one hour from the administering.

In some embodiments, said treating, ameliorating or reduction of at least one depressive symptom persists for at least 12 hours, 24 hours, 36 hours, 48 hours, 72 hours, 96 hours or 1 week. Each possibility represents a separate embodiment of the invention. In some embodiments, aid treating, ameliorating or reduction of at least one depressive symptom persists for at least 24 hours.

In some embodiments, transiently decreasing CaMKII kinase function in a subject comprises administering a CaMKII inhibitor to the subject. In some embodiments, kinase function is decreased in the brain of the subject. In some embodiments, kinase function is decreased in a brain tissue of the subject. In some embodiments, transiently is for not more than 15, 30, 45, 60, 90, 120, 150, or 180 minutes. Each possibility represents a separate embodiment of the invention. In some embodiments, transiently is for not more than 30 minutes. In some embodiments, transiently is for between 15 and 30, 15 and 45, 15 and 60, 15 and 90, 15 and 120, 15 and 150, 15 and 180, 30 and 45, 30 and 60, 30 and 90, 30 and 120, 30 and 150, 30 and 180, 45 and 60, 45 and 90, 45 and 120, 45 and 150, or 45 and 180 minutes. Each possibility represents a separate embodiment of the invention In some embodiments, the methods of the invention further comprise administering to the subject a CaMKII activator at least 15 minutes, 30 minutes, 45 minutes, 1 hour, 90 minutes, or 2 hours after administering the inhibitor. Each possibility represents a separate embodiment of the invention. In some embodiments, the methods of the invention further comprise administering to the subject a CaMKII activator at least 30 minutes after administering the inhibitor. In some embodiments, the methods of the invention further comprise administering to the subject a CaMKII activator at between 15 and 30, 15 and 45, 15 and 60, 15 and 90, 15 and 120, 15 and 150, 15 and 180, 30 and 45, 30 and 60, 30 and 90, 30 and 120, 30 and 150, 30 and 180, 45 and 60, 45 and 90, 45 and 120, 45 and 150, or 45 and 180 minutes after administering the inhibitor. Each possibility represents a separate embodiment of the invention. In some embodiments, the methods of the invention further comprise administering to the subject a CaMKII activator at between 30 and 45 minutes after administering the inhibitor.

In some embodiments, increasing CaMKII kinase function in a subject comprises administering a CaMKII activator to the subject. In some embodiments, the CaMKII kinase function is increased to basal or starting levels. In some embodiments, the CaMKII kinase function is increased to a level greater than the basal level. In some embodiments, the basal level is the level before or at the beginning of performing the method of the invention. In some embodiments, kinase function is increased in the brain of the subject. In some embodiments, kinase function is increased in a brain tissue of the subject. In some embodiments, the increasing is performed not more than 15, 30, 45, 60, 90, 120, 150, or 180 minutes after the decreasing. Each possibility represents a separate embodiment of the invention. In some embodiments, the increasing is performed not more than 30 minutes after the decreasing. In some embodiments, the increasing is performed at least 15, 30, 45, 60, 90, 120, 150, or 180 minutes after the decreasing. Each possibility represents a separate embodiment of the invention. In some embodiments, the increasing is performed at least 30 minutes after the decreasing. In some embodiments, the increasing is performed between 15 and 30, 15 and 45, 15 and 60, 15 and 90, 15 and 120, 15 and 150, 15 and 180, 30 and 45, 30 and 60, 30 and 90, 30 and 120, 30 and 150, 30 and 180, 45 and 60, 45 and 90, 45 and 120, 45 and 150, or 45 and 180 minutes after the decreasing. Each possibility represents a separate embodiment of the invention.CaMKII activators are known in the art and activate the kinase function of CaMKII. In some embodiments, a CaMKII activator increases activating phosphorylation of CaMKII. In some embodiments, an activating phosphorylation comprises phosphorylation of threonine 286 of CAMK2A. In some embodiments, activating phosphorylation comprises phosphorylation of a homologous amino acid to threonine 286 of CAMK2A. In some embodiments, the increase is at least a 10%, 20%, 30%, 40%, 50%, 60%, 70%, 80%, 90%, or 100% increase. Each possibility represents a separate embodiment of the invention.

In some embodiments, the reduction in dosage of ketamine administered to a subject in need thereof is at least a 10%, 20%, 30%, 40%, 50%, 60%, 70%, 80%, 90%, 95%, 99%, or 100% reduction. In some embodiments, the dosage of ketamine is reduced to zero and the CaMKII inhibitor replaces ketamine as the treatment used. In some embodiments, a CaMKII inhibitor reduces the frequency of dosing with ketamine. One skilled in the art will understand that a dosing schedule can be modified to administer a small dose at each dosing time or can be modified to increase the interval between each dose, or a combination of the two.

In some embodiments, increasing CaMKII function, or administering a CaMKII activator increases GluA1 expression in the subject. In some embodiments, the increase in GluA1 expression is after at least 1, 2, 3, 4, 6, 12, 24, or 48 hours. Each possibility represents a separate embodiment of the invention. In some embodiments, the increase is in the brain of the subject. In some embodiments, the increase is in a brain tissue of he subject. In some embodiments, the increase in GluA1 persists for at least 1, 2, 3, 4, 5, 6, or 7 days. Each possibility represents a separate embodiment of the invention. In some embodiments, the increase in GluA1 expression confers long-lasting effect to the treatment. In some embodiments, the treatment or amelioration of depression persists for at least 1, 2, 3, 4, 5, 6, 7 or 14 days. Each possibility represents a separate embodiment of the invention. In some embodiments, the treatment or amelioration of depression persists for at least 1 week.

By another aspect, there is provided a use of a CaMKII inhibitor for treating or ameliorating depression in a subject in need thereof. By another aspect, there is provided a use of a CaMKII inhibitor for reducing the dose of ketamine administered to a subject in need thereof. By another aspect, there is provided a use of a CaMKII inhibitor and a CaMKII activator to treat or ameliorate depression or reduce the dose of ketamine administered to a subject in need thereof. In some embodiments, the CaMKII inhibitor and CaMKII activator are for sequential administration.

By another aspect, there is provided a kit comprising: a CaMKII inhibitor and a CaMKII activator. In some embodiments, the kit is for treating or ameliorating depression or reducing the dose of ketamine administered to a subject in need thereof. In some embodiments, the CaMKII inhibitor and CaMKII activator are for sequential administration.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as weight, is to be understood to include any integer within the recited range, unless otherwise indicated.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989);

Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Animals eEF2 Kinase knockout mice (eEF2K KO; eEF2K-/-) were generated by the laboratory of Christopher Proud. By using heterozygous mice (eEF2K+/-) for breeding, wild-type (eEF2K WT) and knock-out (eEF2K-/-) littermates were derived. C57BL/6 wildtype mice were obtained from local vendors (Harlan, Rehovot, Israel) and after acclimation to the facility were used for experiments. All the mice used in this study were 3-5 months of age and all the experiments were conducted during the light phase of the day (7 am-7 pm).

Reagents and Antibodies

TatCN21 and the respective control peptide (Tatcont) were purchased from GL Biochem (Shanghai, China). Ketamine was obtained from Richter Pharma AGWELS (Austria). Primary Antibodies used were: CaMKIIα (1:25,000; Santa Cruz Biotechnology, SCBT), pT286CaMKIIα (1:1000; SCBT), pT305CaMKIIα (1:1000; Novus biological), GluA1 (1:1000; Abcam or SCBT), pS831GluA1 (1:5000; Epitomics), eEF2 (1:1000; Cell Signaling Technology), peEF2 (1:1000; Cell Signaling Technology), BDNF (1:500; SCBT), BDNF (1:500; Sigma), eIF2α (1:1000; Cell Signaling Technology), peIF2α (1:1000; Cell Signaling Technology) and β-actin (1:3000; SCBT). Secondary antibodies conjugated with HRP (horse radish peroxidase) used were: goat anti-rabbit (IgG), goat anti-mouse (IgG) or rabbit anti-goat (IgG) (1: 10,000; Millipore Bioscience Research Reagents).

SUnSET

Protein synthesis was measured by the SUnSET method. After pharmacological manipulation, mice were sacrificed by cervical dislocation, brains were removed, and the hippocampi were rapidly dissected, immersed in liquid nitrogen, and stored at -80° C. until further use. Hippocampi were homogenized using 20 strokes of a pre-chilled glass homogenizer with 600 µl of lysis buffer containing 50 mM Tris, pH 7.8, 240 mM KCl, 10 mM MgCl2, 250 mM D-sucrose, 2% Triton X-100, 20 µg/ml emetine, 5 mM DTT, 100 U/ml Rnasin (Promega), and protease inhibitor mixture without EDTA (Roche). Samples were centrifuged for 5 min at 16,100 g at 4° C. and supernatant was incubated with 100 g/ml puromycin for 10 min at 4° C. An equal volume of 2×SDS sample buffer (10% glycerol, 5% β-mercaptoethanol, 4% SDS, 120 mM Tris-HCl, pH 6.8) was added to the samples and then boiled for 10 min at 100° C. Protein concentrations were determined using the BCA protein assay (Thermo), and samples were stored at -20° C. until further use. Puromycin incorporation was detected by western blotting using 12D10 antibody for puromycin (1:1000, Millipore).

Western Blotting

Sample preparation: Brains were quickly excised; hippocampus and cortex were dissected, and snap frozen in liquid nitrogen. Tissues were transferred from the liquid nitrogen to a glass-Teflon homogenizer and homogenized with a buffer containing 10 mM HEPES pH 7.4, 2 mM EDTA, 2 mM EGTA, 0.5 mM DTT (all from Sigma), 1× phosphatase inhibitor mixture (Sigma/Thermo Scientific), and 1× protease inhibitor mixture (Sigma/Thermo Scientific). Equal volumes of 2×SDS sample buffer were immediately added to the homogenates, and samples were boiled for 10 min. Samples were centrifuged at 12,000 g for 15 minutes and the supernatants were transferred to 3 aliquots. Each aliquot was thawed on ice and used for blotting only once or twice.

Prepared samples in SDS sample buffer were subjected to 7.5% or 4-20% gradient gel (Bio-Rad pre-cast gels) SDS-PAGE (electrophoresed on Bio-Rad PAGE apparatus) and Western blot analysis. Each sample was loaded with the same amount of total protein (7-15 µg; according to antibody linearity). After transfer to a 0.2 µm pore size nitrocellulose or polyvinyidine fluoride membranes, the blots were blocked with 4% bovine serum albumin (BSA) or 4% non-fat dry milk in tris-buffered saline plus 0.5% tween-20 (TBST) at room temperature for 1 hr. They were then incubated overnight with the suitable primary antibodies at 4° C. The blots were then subjected to three 10 min washing steps in TBST, after which they were incubated with the corresponding HRP-conjugated secondary antibodies for 1h at room temperature followed by three 10 min washing steps with TB ST. Immunodetection was performed with the enhanced-chemiluminescence EZ-ECL kit (Biological Industries, Israel). The immunoblots were quantified with a CCD camera and Quantity One software (Bio-Rad). Each immunoblot was measured relative to the background and normalized to the endogenous controls (β-actin). Phosphorylation levels were calculated as the ratio between the readings from the antibody directed against the phosphoproteins and those from the antibody directed against the phosphorylation state-independent forms of the proteins.

Forced Swim Test (FST)

After receiving treatments mice were subjected to FST. Briefly, mice were introduced into a transparent glass beaker (26 cm×18 cm) containing 4 liters deep water at 24° C. and were video-recorded for 6 minutes. The last 4 min were scored for immobility. Total immobility time (in seconds) is shown in the results.

Tail Suspension Test

Custom made clear hollow cylinders (4 cm length, 1.2 cm inner diameter, 1 g) from polycarbonate tubing were placed around the tails of mice to prevent tail climbing behavior. Tape was adhered to the tails of mice on one end, and the other end of the tape was adhered to a custom designed chamber with a white background. Mice were video recorded for 6 minute and the entire 6 minute session was scored for immobility. Total immobility time (seconds) is shown in the results.

Novelty Suppressed Feeding (NSF)

After receiving the treatments mice were subjected to NSF. Briefly, mice were food deprived for 14 h and then placed in a temporary home cage for 30 min. During the test, mice were placed in a square arena 50×50 cm with bright room light. A food pellet was placed in the center of an open field. Each trial was 10 min in duration. Animal behavior was recorded, and latency to feeding (s) was measured.

Statistical Analysis

Statistical analyses were done with IBM SPSS Statistics software. Graphs were generated with Microsoft excel worksheet software. Differences among multiple groups were assessed by One-Way or Two-Way ANOVA and LSD post-hoc tests. Independent samples t-test with two-tail was conducted when two groups (saline vs ketamine) were compared. Null hypothesis was rejected at the 0.05 level. Number (N) of mice for all statistical analyses is indicated in the main text.

Phospho-Proteomics

Reduction, Alkylation, and Tryptic Digestion

Sample preparation: Hippocampus and cortex were dissected out and snap frozen in liquid nitrogen and stored at −80° C. until further use. Samples were homogenized using a plastic hand-held motor driven homogenizer with freshly prepared 8 M urea solution (Sigma-Aldrich). The concentration of proteins in samples was quantified using Bradford's protein assay (Bio-Rad). Samples containing 1 mg/ml protein were prepared, aliquoted, and stored at −80° C. until further use. Proteins were reduced with 10 mM dithiothreitol (DTT) for 1 h at 56° C., alkylated with 50 mM iodoacetamide for 1 h at room temperature (RT), and diluted by fourfold to less than 1 M urea with 100 mM ammonium acetate at pH 8.9. Proteins were digested using sequencing grade trypsin (Promega; 1 µg trypsin per 50 µg protein) overnight at RT. Enzyme activity was quenched by acidification of the samples with acetic acid. The peptide mixture was desalted and concentrated on a C18 Sep-Pak Plus cartridge (Waters) and eluted with 50% acetonitrile/0.1% formic acid and 0.1% acetic acid. Solvent was evaporated in a SpeedVac vacuum centrifuge. Samples were aliquoted to 400 m and frozen in liquid nitrogen for 5 min, lyophilized, and stored at −80° C.

Tandem Mass Tag (TMT) Labeling

Lyophilized peptides were labeled with TMT-6-plex Mass Tag labeling kits (Thermo). For each TMT multiplex, a pooled sample was included, consisting of a combination of equal amounts of peptides from Tatcont and TatCN21 treated mice, allowing for relative quantification to a normalization channel. For TMT labeling, 5 peptide aliquot samples from 5 mice and one normalization channel (400 µg peptide for each channel) were resuspended in 100 µL of 70% (vol/vol) ethanol, 30% (vol/vol) 0.5 M triethyl-ammoniumbicarbonate at pH 8.5 and incubated with TMT reagent resuspended in 40 µL anhydrous acetonitrile at RT for 1 h. The samples were concentrated, combined, and concentrated to dryness using a SpeedVac vacuum centrifuge.

Peptide Fractionation

The TMT-labeled peptide pellet was fractioned via high-pH reverse phase HPLC. Peptides were resuspended in 100 µL buffer A (10 mM TEAB, pH8) and separated on a 4.6 mm×250 mm 300Extend- C18, 5 µm column (Agilent) using a 90-minute gradient with buffer B (90% MeCN, 10 mM TEAB, pH8) at a flow rate of 1ml/min. The gradient was as follows: 1-5% B (0-10 min), 5-35% B (10-70 min), 35-70% B (70-80 min), 70% B (80-90 min). Fractions were collected over 75 minutes at 1 minute intervals from 10 min to 85 min. The fractions were concatenated into 6 fractions non-contiguously (1+16+31+46+61, 2+17+32+47+62, etc). The fractions were concentrated to near dryness using a Speed-Vac vaccum centrifuge (Thermo Scientific Savant).

Phosphopeptide Enrichment

Phosphopeptides were enriched from each of the 15 fractions using the High-Select Fe-NTA phosphopeptide enrichment kit (Thermo) according to manufacturer's instructions.

Liquid Chromatography-Tandem Mass Spectrometry (LC-MS/MS)

Peptides were separated by reverse phase HPLC (Thermo Easy nLC1000) using a precolumn (made in house, 6 cm of 10 µm C18) and a self-pack 5 µm tip analytical column (12 cm of 5 µm C18, New Objective) over a 140 minute gradient before nanoelectrospray using a QExactive Plus mass spectrometer (Thermo). Solvent A was 0.1% formic acid and solvent B was 80% MeCN/0.1% formic acid. The gradient conditions were 0-10% B (0-5 min), 10-30% B (5-105 min), 30-40% B (105-119 min), 40-60% B (119-124 min), 60-100% B (124-126 min), 100% B (126-136 min), 100-0% B (136-138 min), 0% B (138-140 min), and the mass spectrometer was operated in a data-dependent mode. The parameters for the full scan MS were: resolution of 70,000 across 350-2000 m/z, AGC 3e6, and maximum IT 50 ms. The full MS scan was followed by MS/MS for the top 10 precursor ions in each cycle with a NCE of 34 and dynamic exclusion of 30 s. Raw mass spectral data files (.raw) were searched using Proteome Discoverer (Thermo) and Mascot version 2.4.1 (Matrix Science). Mascot search parameters were: 10 ppm mass tolerance for precursor ions; 15 mmu for fragment ion mass tolerance; 2 missed cleavages of trypsin; fixed modifications were carbamidomethylation of cysteine and TMT 6plex modification of lysines and peptide N-termini; variable modifications were methionine oxidation, tyrosine phosphorylation, and serine/threonine phosphorylation. TMT quantification was obtained using Proteome Discoverer and isotopically corrected according to manufacturer's instructions and were normalized to the mean of each TMT channel. Only peptides with a Mascot score greater than or equal to 25 and an isolation interference less than or equal to 30 were included in the data analysis.

The washed pre-column was connected in series with an in-house packed analytical capillary column [50 µm ID×12 cm packed with 5 µm C18 beads (YMC gel, ODSAQ, 12 nm, S-5 µm, AQ12S05)] with an integrated electrospray tip (~1 µm orifice). Peptides were eluted using a 140 min (phosphopeptides) or 90 min (total peptide) gradient from 9 to 70% acentonitrile in 0.2M acetic acid at a flow rate of 0.2 ml/min, with a flow split of 10,000:1, yielding a final electrospray flow rate of ~20 nL/min. A total of 15 fractions from each sample was collected. Phosphopeptides were analyzed using a Thermo Q Exactive Hybrid Quadrupole-Orbitrap Plus mass spectrometer with the following settings: spray voltage, 2 kV; no sheath or auxiliary gas flow, heated capillary temperature, 250° C.; S-lens radio frequency level of 50%. The Q Exactive was operated in data-dependent acquisition mode. Full-scan MS spectra [mass/charge ratio (m/z), 350 to 2000; resolution, 70,000 at m/z 200] were detected in the Orbitrap analyzer after accumulation of ions at 3e6 target value based on predictive AGC from the previous scan. For every full scan, the 15 most intense ions were isolated (isolation width of 0.4 m/z) and fragmented (collision energy (CE): 32%) by higher-energy collisional dissociation (HCD) with a maximum injection time of 300 ms and 35,000 resolutions. Total peptide analysis was performed on an LTQ Orbitrap XL mass spectrometer with the following settings: spray voltage, 2 kV; no sheath or auxiliary gas flow, heated capillary temperature, 250° C. Analysis was performed in a data-dependent acquisition mode; full-scan mass spectra (m/z range 400-2000, resolution 60,000)

were detected in the Orbitrap analyzer (ion target value $5\times10^5$). For every full scan, the 10 most intense ions were isolated (isolation width 3 Da) and fragmented by HCD (CE: 75%) in the HCD cell followed by detection in the Orbitrap (ion target value $1\times10^5$) for iTRAQ marker ion quantification.

Mass Spectrometry Peptide Mapping Data Analysis

Raw mass spectral data files were loaded into Proteome Discoverer version 1.4.1.14 (DBversion: 79) (Thermo) and searched against the mouse SwissProt database using Mascot version 2.4 (Matrix Science). TMT reporter quantification was extracted, and isotope corrected in Proteome Discoverer. Tandem mass spectra were matched with an initial mass tolerance of 10 ppm on precursor masses and 15 mmu for fragment ions. Cysteine carbamidomethylation, TMT-labeled lysine and protein N-terminal were searched as fixed modifications. Oxidized methionine, and phosphorylation of serine, threonine, and tyrosine were searched as variable modifications. Minimal peptide length was seven amino acids. The data sets were filtered by ion score>20 for all peptides to ensure high confidence in peptide identification and phosphorylation localization and to achieve an (FDR) below 1% for peptides. Phosphopeptide quantification was normalized based on median relative peptide quantification obtained from the crude peptide analysis to correct for slight variation in sample amount among TMT-channels. For each phosphopeptide, relative quantification was represented as a ratio between TMT ion intensities from each analyzed sample and the included normalization channel.

Bioinformatics Analysis

To identify differentially phosphorylated peptides with significantly regulated ratios, we chose an arbitrary cutoff of ±15% difference with a P value of <0.05. Thus, subsequent bioinformatic analyses included peptides with ratios <0.84 and >1.16 relative to their normalization channel deemed as downregulated or upregulated, respectively. The non-regulated background pool consisted of peptides with ratios between 0.85-1.15. The name of proteins from protein accession numbers were converted to gene list using Uniprot ID mapping retrieval tool. All active interaction sources except text mining were included, and to ensure high confidence, a confidence score over 0.9 was required. Molecular function analysis term enrichment analysis was first performed on terms related to biological process using the STRING and TopGene bioinformatics resources, and later was manually filtered to look for the commonly present from these three resources. Significance was concluded when $P<0.05$ by Fisher's exact test.

Example 1

Ketamine Administration Regulates Both CaMKII and eEF2 Pathways in the Brain

To explore the interplay between the eEF2 pathway and CaMKII in the context of depression, ketamine was injected intraperitoneally (IP) into normal C57BL/6 mice at a dose of 5 mg per kg body weight (b.w.), and its production of an anti-depressant effect in a depressive situation was investigated via the forced swim test (FST).

Indeed, consistent with the literature, it was observed that ketamine administration reduced the immobility time in the forced swim test (FIG. 1A). Reduced phosphorylation of eEF2 after ketamine administration is well reported as mediating the anti-depressant action of ketamine. These major findings were replicated, as 20 min after ketamine administration, eEF2 phosphorylation, but not he protein itself, was significantly reduced,) (FIGS. 1B-1C) in the hippocampus.

Figure 1B:
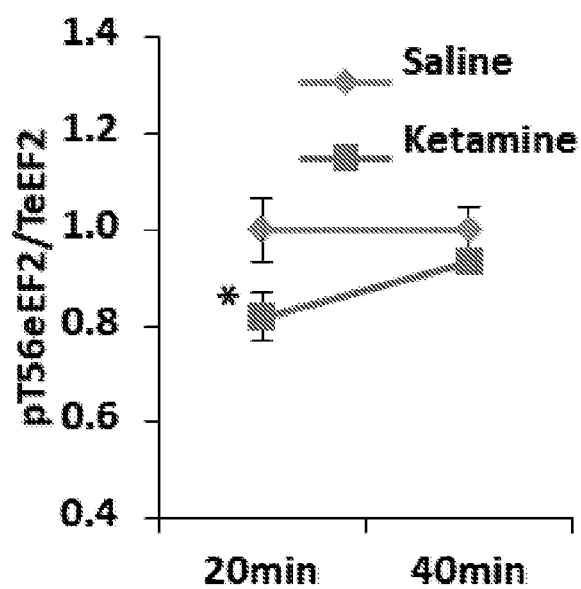
Figure 1C:
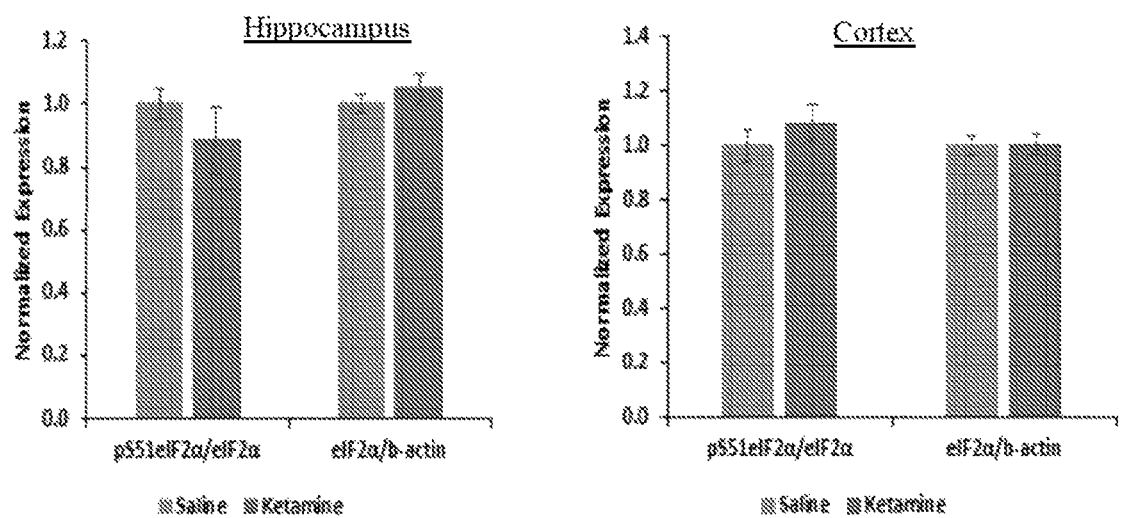
Figure 1D:
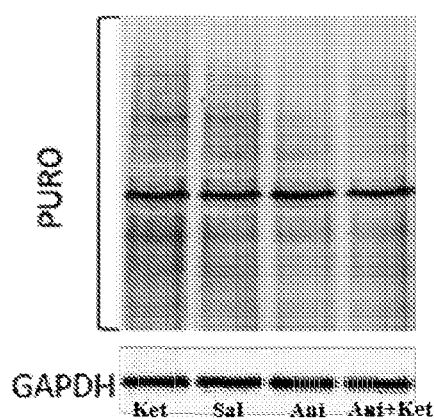
Figure 1E:
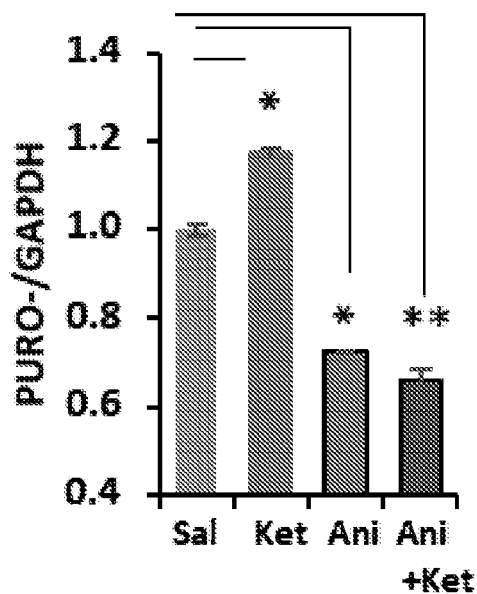

Reduced phosphorylation is associated with an increased elongation phase of protein synthesis. Therefore, whether ketamine administration increases global protein synthesis was investigated next (FIG. 1D). Remarkably, protein synthesis was significantly increased in the hippocampus 30 minutes after ketamine injection (FIG. 1E). Administration of the protein synthesis, inhibitor, anisomycin (120 mg/kg b.w.), which inhibits peptidyl transferase, blocked protein synthesis. Interestingly ketamine-induced protein synthesis was also blocked by anisomycin (FIG. 1E).

Figure 1F:
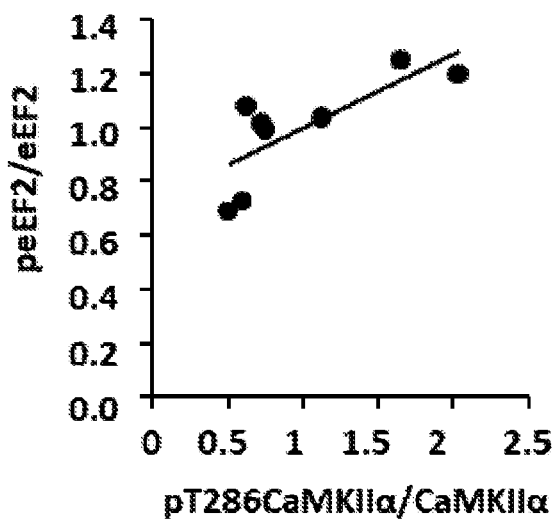
Figure 1G:
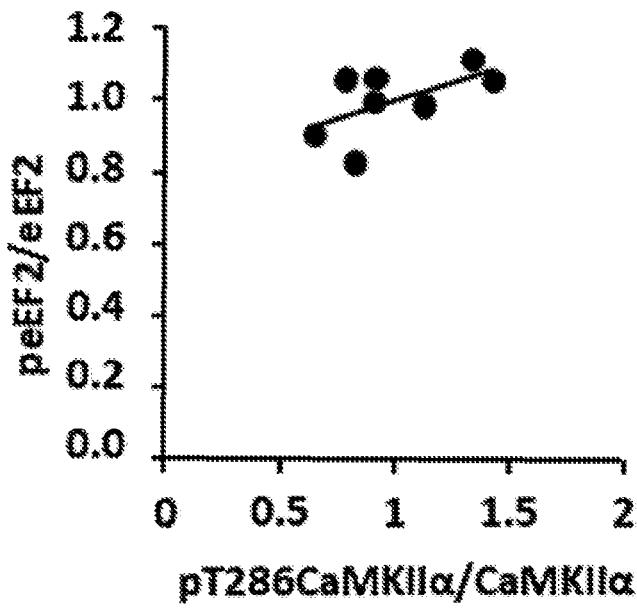
Figure 1H:
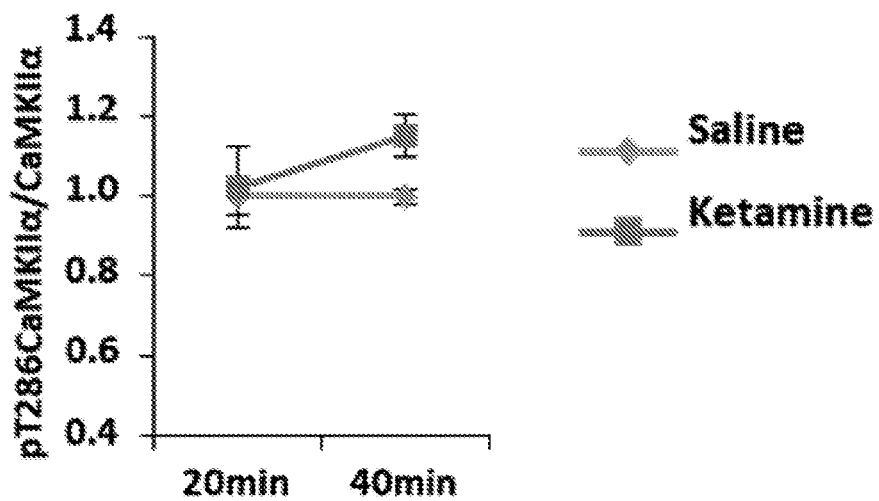
Figure 1I:
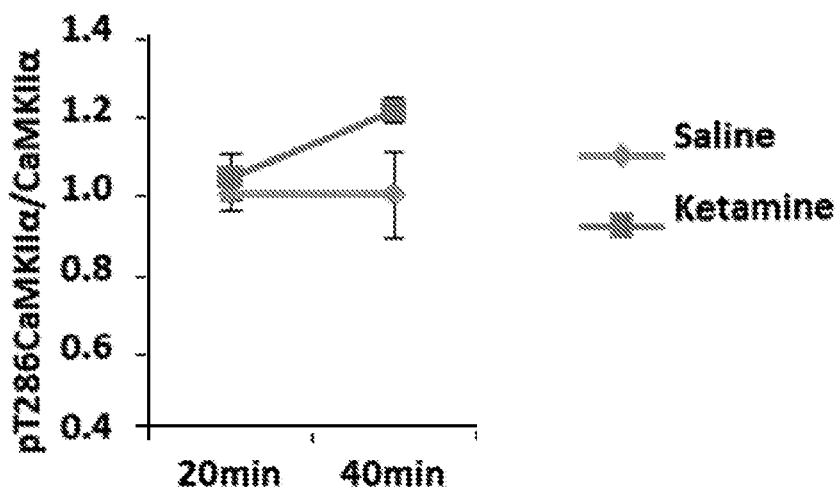

It is not known whether the phosphorylation status of different calcium/calmodulin-dependent kinases (CaMKs), which determines their activity, is correlated under baseline conditions and/or following neuronal activity in the brain. It was found that pT286-CaMKIIα and pT56-eEF2 are well correlated in both hippocampal (FIG. 1F) and cortical (FIG. 1G) lysates from C57BL/6 mice. Given this observation, and the decrease in pT56-eEF2 following ketamine administration (FIG. 1B), it was next asked how CaMKII is modulated following ketamine administration. Interestingly, it was observed that auto-active phosphorylation of CaMKIIα (pT286) was slightly increased 40 min after ketamine injection both in the hippocampus ((FIG. 1H), and in the cortex (FIG. 1I). By contrast, auto-inhibitory phosphorylation of CaMKIIα (pT305) showed significant induction at 20 min in the hippocampus (FIG. 1J), and the cortex (FIG. 1K), and returned to baseline at the 40 minute time point, suggesting that there is possibly a net inhibition of the function of CaMKII 20 minutes after ketamine administration. Total CaMKIIα did not show any difference at any time point examined (FIGS. 1L and 1M respectively). Together, these data led one to reason that CaMKII, in addition to eEF2 and its downstream signaling, contributes to the antidepressant properties of ketamine.

Example 2

Figure 2A:
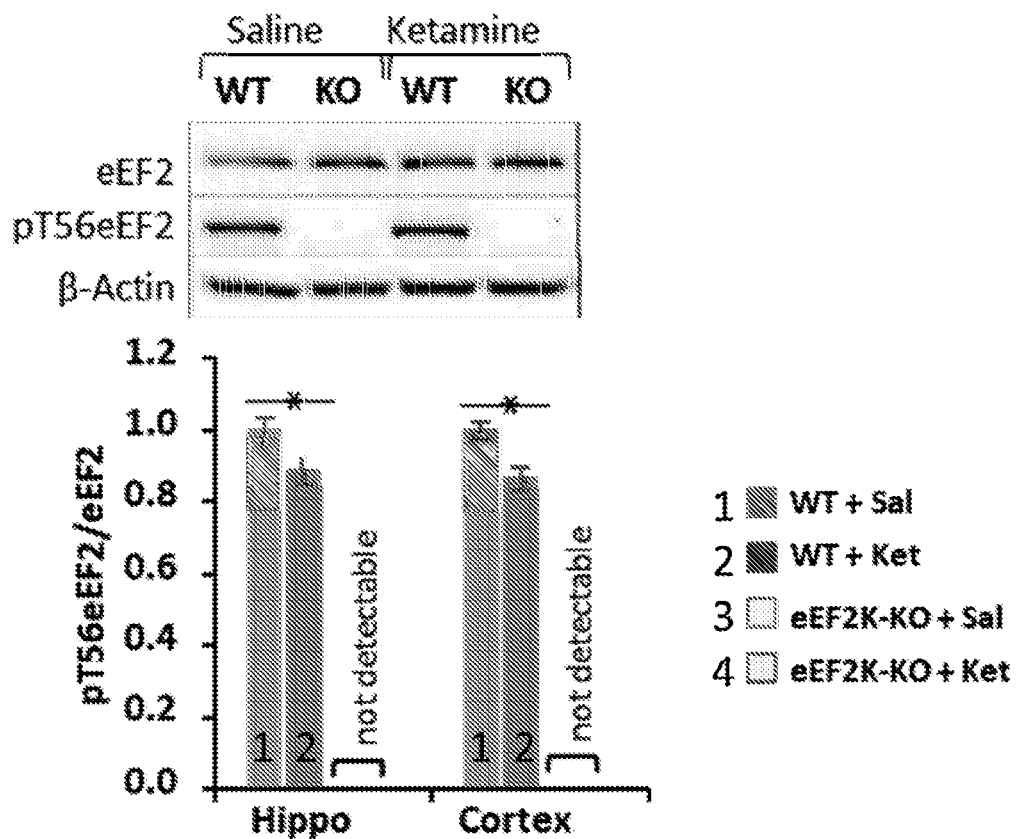
FIGS. 2A-2E. eEF2 mediates ketamine-induced anti-depression, as well as global protein synthesis. (2A) (Top) Representative immunoblots from WT and eEF2K-KO mice 30 minutes after saline or ketamine administration. (Bottom) Bar graph quantification of the protein levels in the immunoblots. (2B) Bar graph of total protein levels measured via the SUnSET method. (2C) Bar chart showing relative expression of pT286CaMKIIα, and pT305CaMKIIα. (2D) Bar graph of immobility time in the FST 30 minutes after ketamine administration. (2E) Bar chart showing the total velocity expressed in cm/s for 4 minutes during the FST.

Acute Ketamine Treatment and Permanent Genetic Deletion of eEF2K Demonstrate Similar Molecular Readouts Next, the effect of knocking out eEF2K on forced swim behavior, CaMKII signaling, and protein synthesis following ketamine administration was examined. The hippocampal lysates of eEF2K-KO mice were devoid of phosphorylated eEF2 (peEF2) but displayed normal levels of total eIF2a (FIG. 2A) demonstrating the specificity of the knock-out and further confirming that eEF2K is the only kinase regulating eEF2 phosphorylation on Thr-56. Moreover, it was observed that peEF2 was significantly lower in the WT mice 30 minutes after ketamine administration, which together with FIG. 1B indicates the relatively narrow window of eEF2 phosphorylation: 20-30 minutes after ketamine administration peEF2 is strongly decreased, whereas by 40 minutes it returns to its baseline levels (FIGS. 1B and 2A).

Figure 2B:
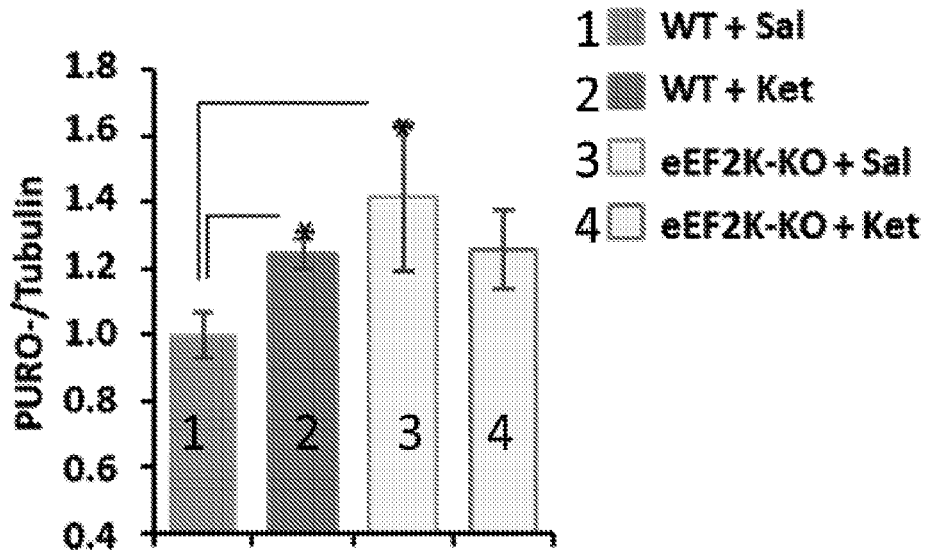

It was further investigated whether eEF2K-KO mice exhibit a significant difference in global protein synthesis (FIG. 2B). It was found that eEFK-KO mice show higher levels of puromycin incorporation compared to WT mice, indicating that knocking out eEF2K leads to increased protein synthesis. Moreover, consistent with the results shown in FIGS. 1D and 1E, it was observed that ketamine administration increased protein synthesis in WT mice but did not lead to further increase in global protein synthesis in the hippocampus of eEF2K-K) mice (FIG. 2B).

Figure 1J:
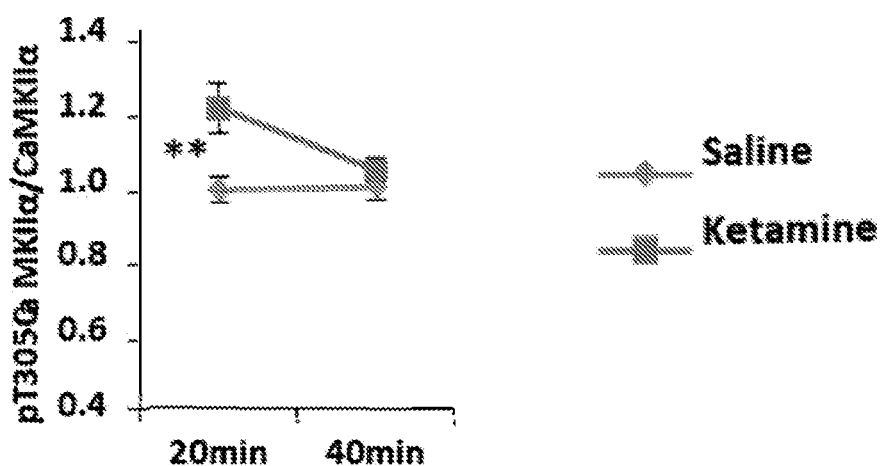
Figure 1K:
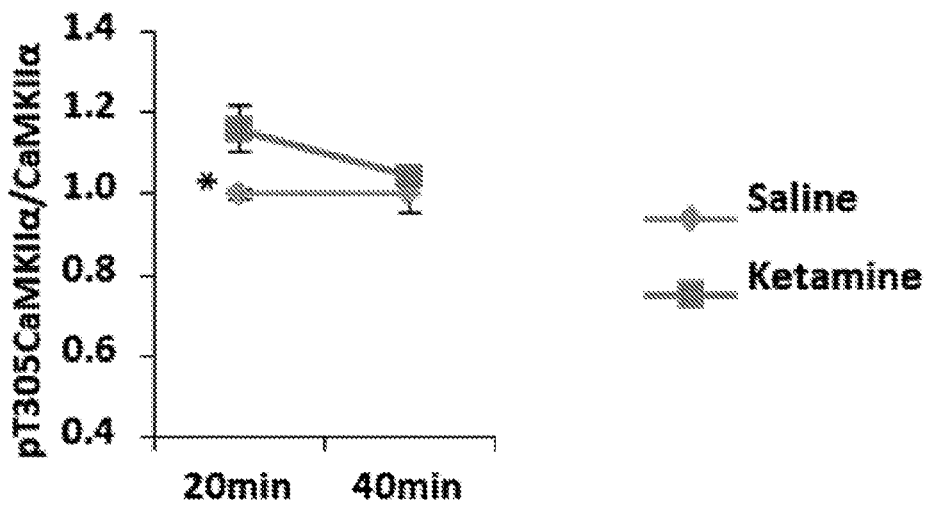
Figure 1L:
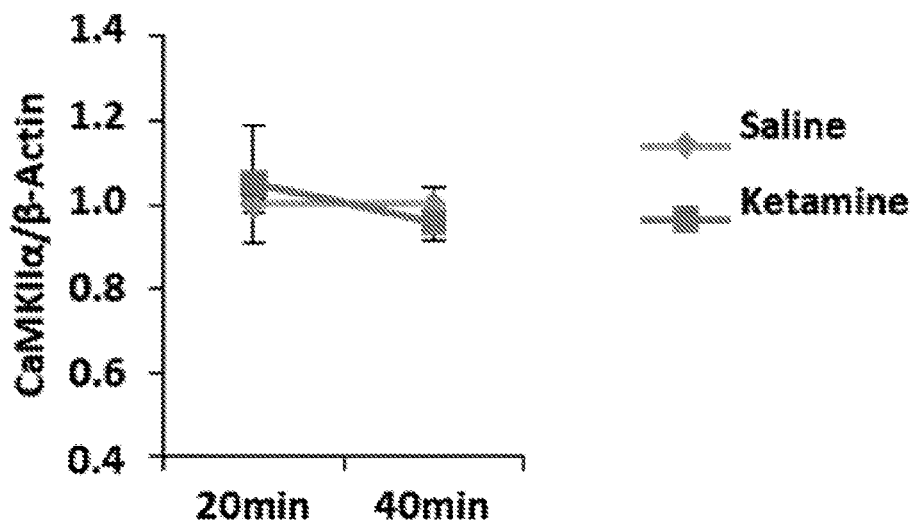
Figure 1M:
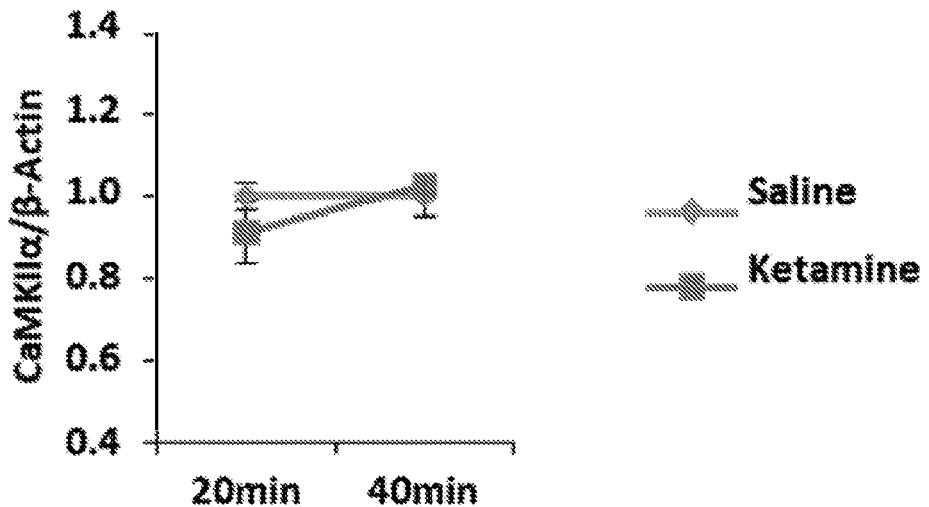
Figure 2C:
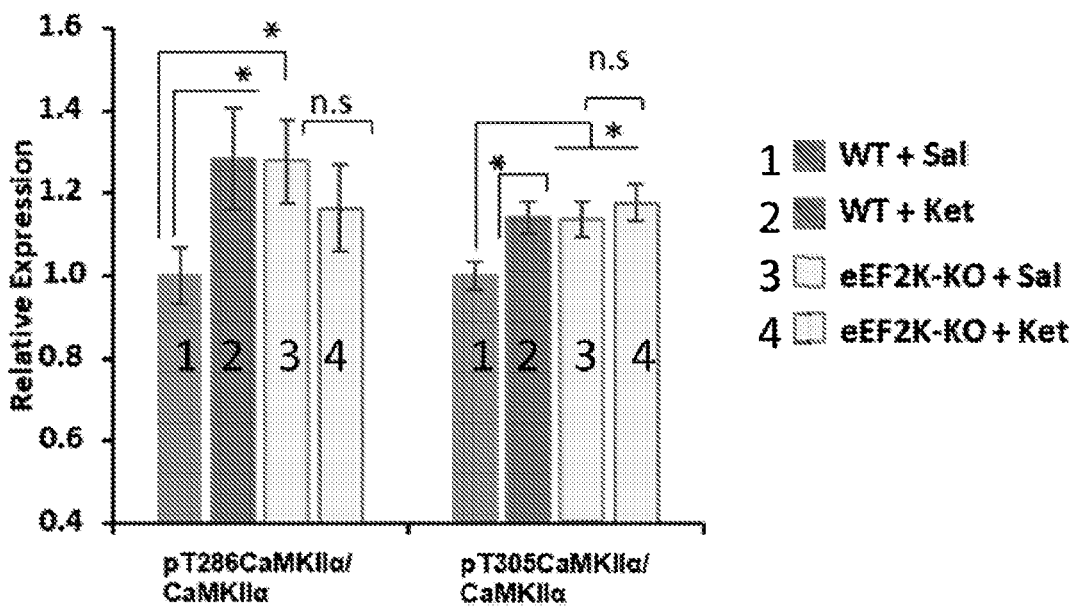

As previously stated, using C57BL/6 mice, a significant induction of pT305CaMKIIα was observed at 20 minutes following administration of ketamine, which returned to baseline levels at the 40 min time point (FIG. 1J-K). With the increased sample size of the WT littermates, it was found that pT305 phosphorylation was significantly higher 30 minutes after ketamine administration. Moreover, pT286CaMKIIα was also higher in WT animals treated with ketamine (FIG. 2C). Interestingly, both pT286 and pT305 phosphorylation levels of CaMKIIα were higher in the eEF2K-KO on a basal level and no additive changes were observed in these mice after ketamine administration. These later results demonstrate that eEF2K can modulate the function of CaMKII. Together, the notable insight here is that although there might be differences in the expression and phosphorylation status of several proteins when eEF2K is knocked out, these changes are compromised under the blockade of NDMAR by ketamine treatment.

Figure 2D:
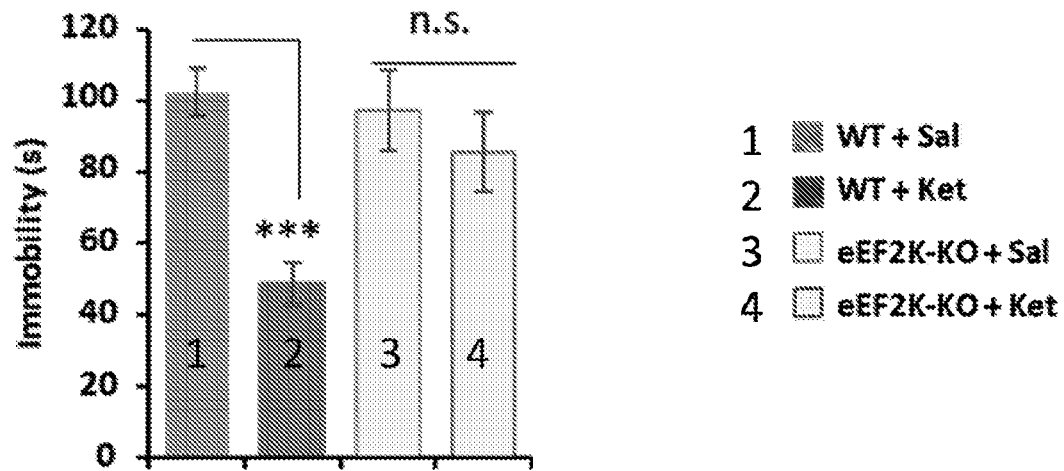
Figure 2E:
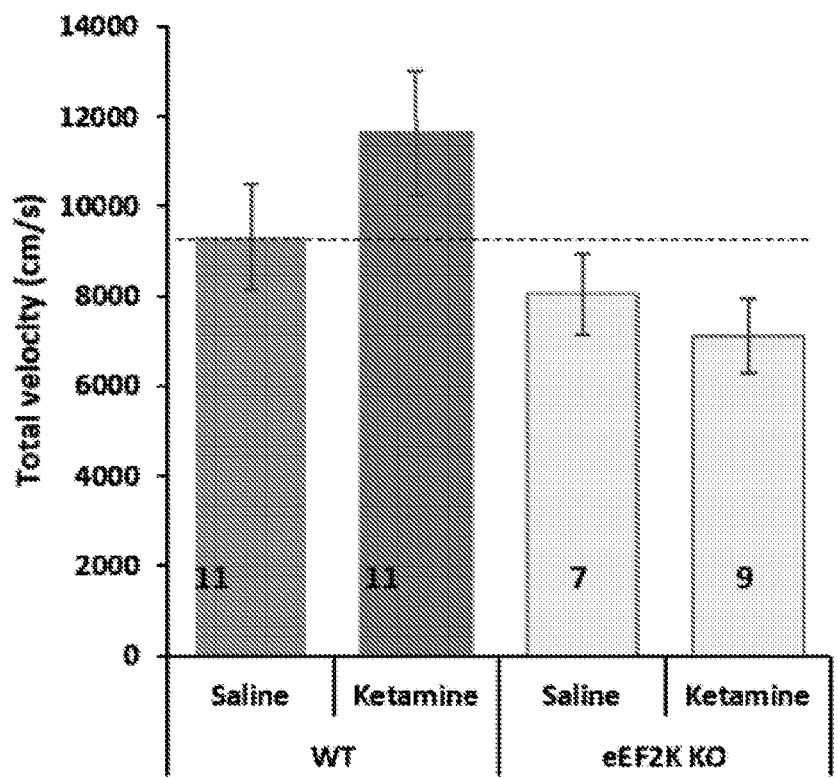

Following the biochemical analysis described above, in order to assess the behavioral anti-depressant effects of ketamine in the absence of eEF2K, eEF2K-KO mice were subjected to the FST paradigm of depression 30 minutes after the administration of ketamine. Ketamine injection reduced the immobility time in WT littermates, whereas in eEF2K-KO mice, no difference in immobility was observed following ketamine administration, suggesting that the genetic deletion of eEF2K blocks the anti-depressant effect of ketamine in this paradigm (FIG. 2D). General locomotor activity by total velocity of movements during the entire last 4 minutes of FST was analyzed to determine if ketamine induces any locomotor impairment that interferes with responses in the FST. No major significant differences between groups was found, suggesting that the difference in immobility state cannot be attributed to changes in swimming speed in the FST (FIG. 2E).

Example 3

Ketamine Administration Induces CaMKII-Dependent GluA1 Expression

Although the auto-inhibitory phosphorylation of CaMKII (pT305) appears to reach baseline levels 40 minutes after the administration of ketamine, the auto-active phosphorylation (pT286) shows an increasing trend. To follow up on this, the phosphorylation status of CaMKII was measured 1 hour after ketamine injection. Interestingly, it was found that ketamine differentially regulates the auto-active and auto-inhibitory phosphorylation of CaMKII. Specifically, pT286CaMKKKa was observed to significantly increase, whereas pT305CaMKIIa was reduced in both the hippocampus and the cortex (FIG. 3A-E), suggesting a net activation of CaMKII and a potential role of CaMKII in the anti-depressant action of ketamine.

Figure 3A:
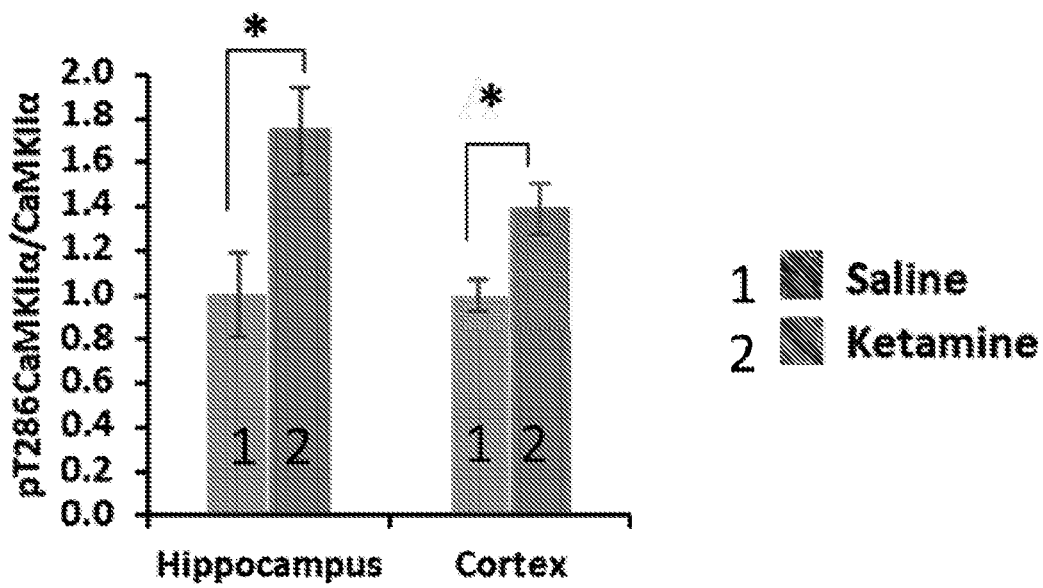
FIGS. 3A-3N. Ketamine regulation of GluA1 is mediated by CaMKII. (3A-3C) Bar chart of (3A) auto-active phosphorylation pT286CaMKIIa levels, (3B) inhibitory phosphorylation pT305CaMKIIa levels and (3C) total CaMKIIa levels in brain tissue collected 1 hour after ketamine administration. (3D-3E) Bar charts of phosphorylation status of CaMKII in (3D) hippocampus and (3E) cortex after injection of saline or 50 mg/kg b.w. ketamine. (3F) Volcano plot showing the differentially phosphorylated proteins with fold difference and p-value between TatCont and TatCN21 groups. (3G) Heatmap showing the different phosphosites from CaMKIIa that were identified. (3H) Gene ontology (GO) terms with p-values for molecular functions associated with the differentially phosphorylated proteins. (3I) Representative immunoblots of brain tissue collected 3 hours after CaMKII inhibitor was injected 10 minutes before ketamine injection. (3J) Bar charts showing relative protein expression in the brain tissue lysates of 3I. (3K) Bar graph showing relative peEF2 levels in hippocampal samples. (3L) Line graph showing GluA1 levels after ketamine injection in the hippocampus. (3M) Representative immunoblots of brain tissue collected 24 hours after CaMKII inhibitor was injected 10 minutes before ketamine injection. (3N) Bar charts showing relative protein expression in the brain tissue lysates of 3M.
Figure 3B:
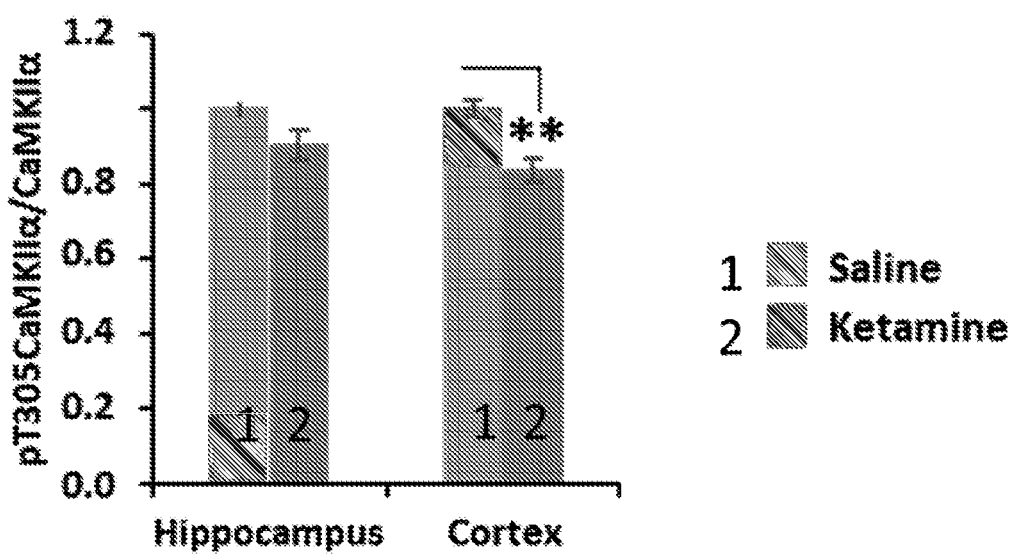
Figure 3C:
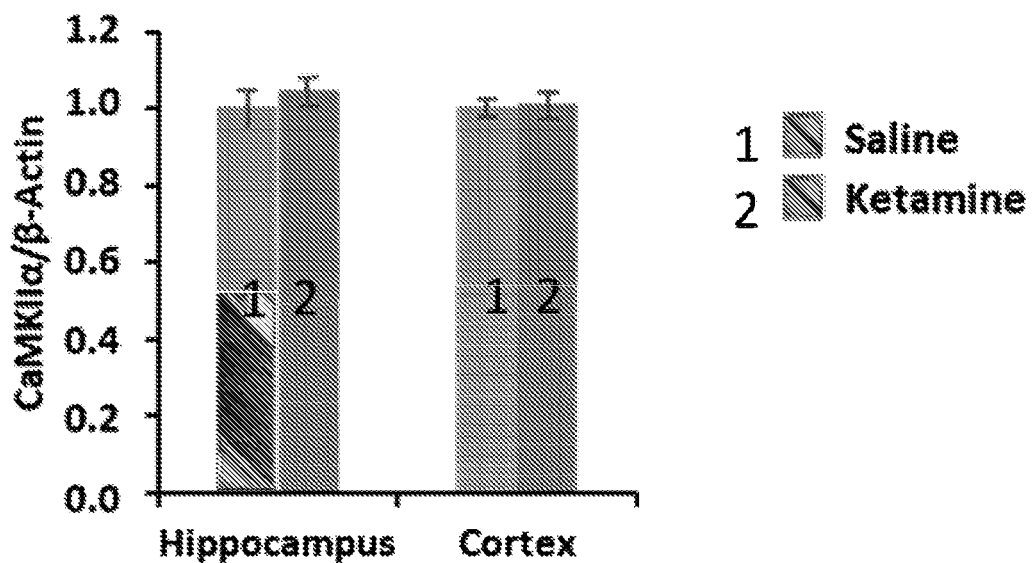
Figure 3D:
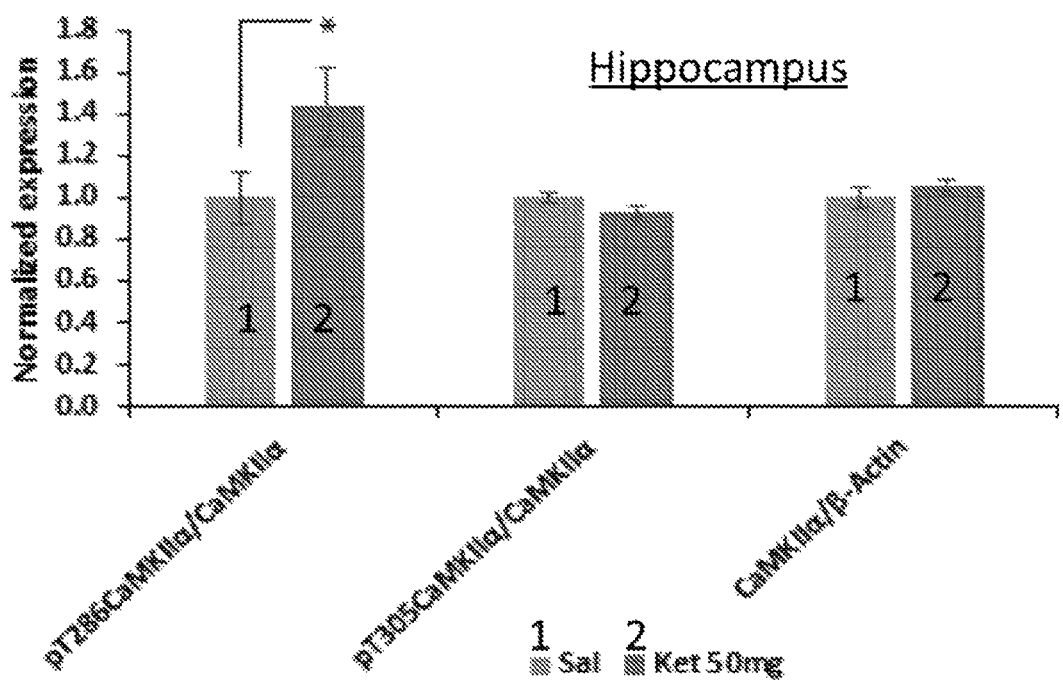
Figure 3E:
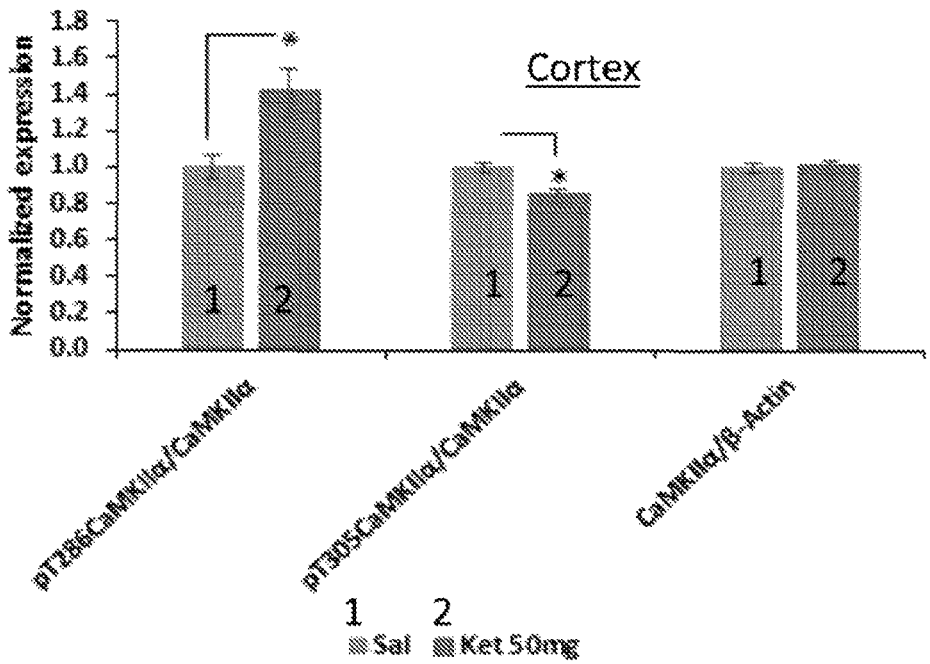
Figure 3F:
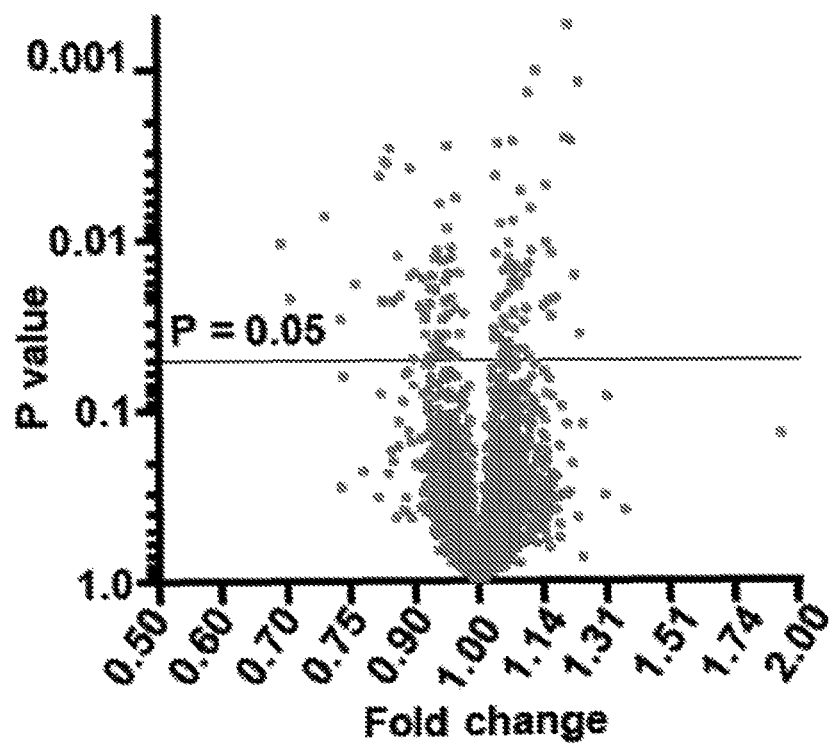
Figure 3G:
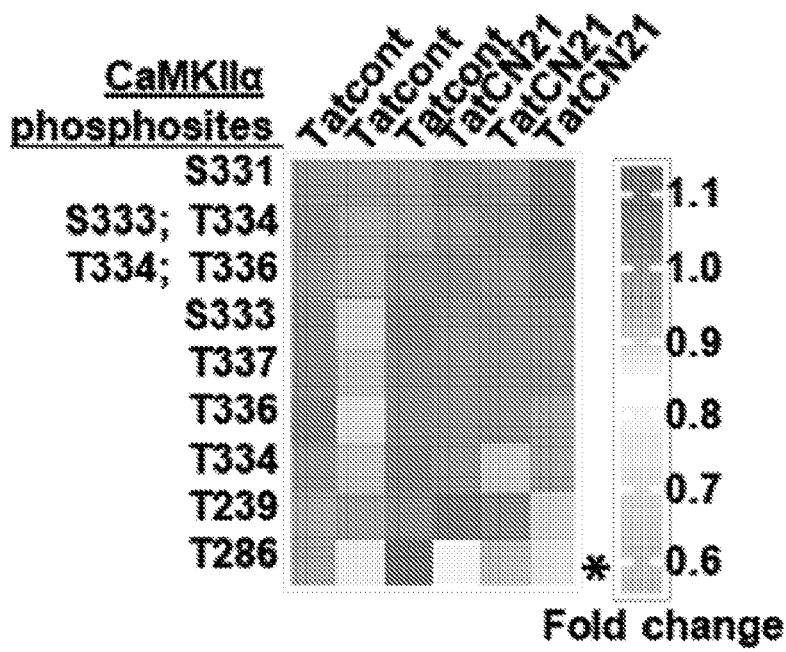
Figure 3H:
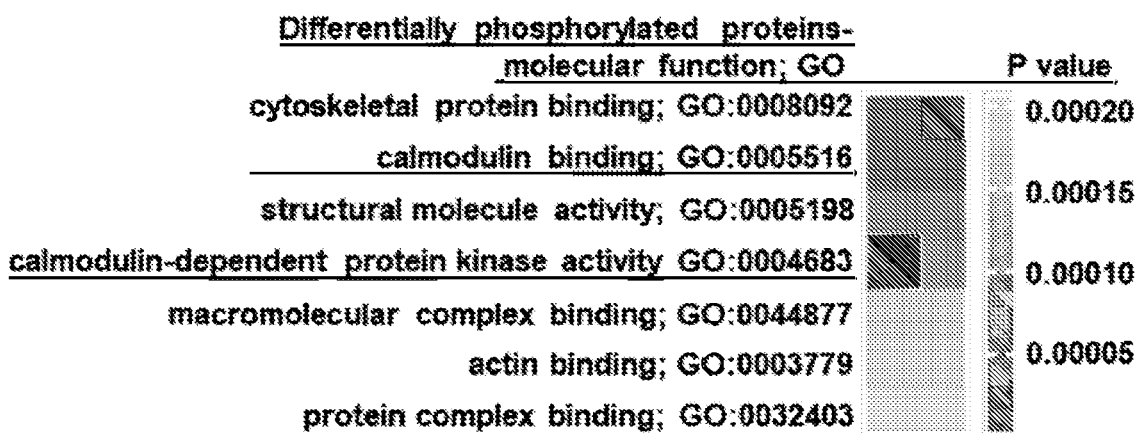

To further explore the role of CaMKII in mediating the anti-depressant action of ketamine, the peptide inhibitor of CaMKIIa, TatCN21, which is derived from the endogenous CaMKIIa inhibitor and consists of the 21 amino acid CN21 peptide fused to the cell permeable peptide Tat, was used. TatCN21 has been previously tested for its efficacy and specificity in vitro. First, TatCN21 or control peptide, Tatcont (5 mg/kg b.w., i.p.), was injected to mice, the hippocampus tissue was collected 30 minutes later, and the tissue was evaluated for the in vivo specificity of TatCN21 by performing global serine/threonine phosphor-proteomics analysis (FIG. 3F). 3061 phosphopeptides from 1307 protein were identified, of which 55 S/T residues were differentially phosphorylated (FIG. 3E). Specifically, CaMKIIa phosphorylation was examined after systemic administration of TatCN21, and nine phosphopeptides from CaMKIIa (S331, S333; T334, T334:T336, S333, T337, T446, T334, T239, and T286) were found. Out of these, TatCN21 significantly reduced T286 CaMKIIa in the hippocampus (FIG. 3G). This finding is consistent with previous in vitro studies. Moreover, auto-active phosphorylation of the CaMKIIβ subunit at the T287 residue also plays a crucial role in controlling CaMKII function. Interestingly, TatCN21 also reduced T287 as well as T321 CaMKIIβ, indicating that TatCN21 overall reduces the auto-active phosphorylation status of the CaMKII holoenzyme. Next, the molecule function analysis was performed using all 55 differentially phosphorylated protein after TatCN21, and it was found that calmodulin and calmodulin-dependent kinase bindings were significantly associated with these proteins (FIG. 3H), and this correlates with the overall effect of TatCN21 on CaMKII.

Figure 3I:
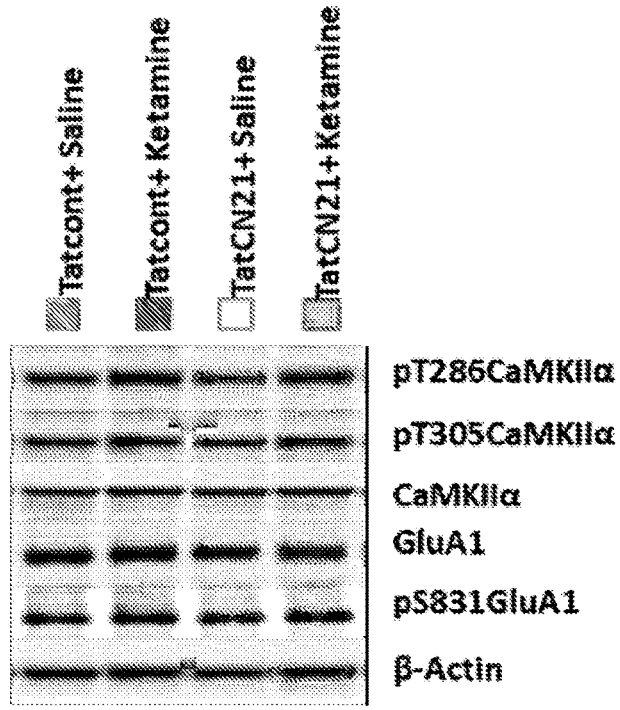
Figure 3J:
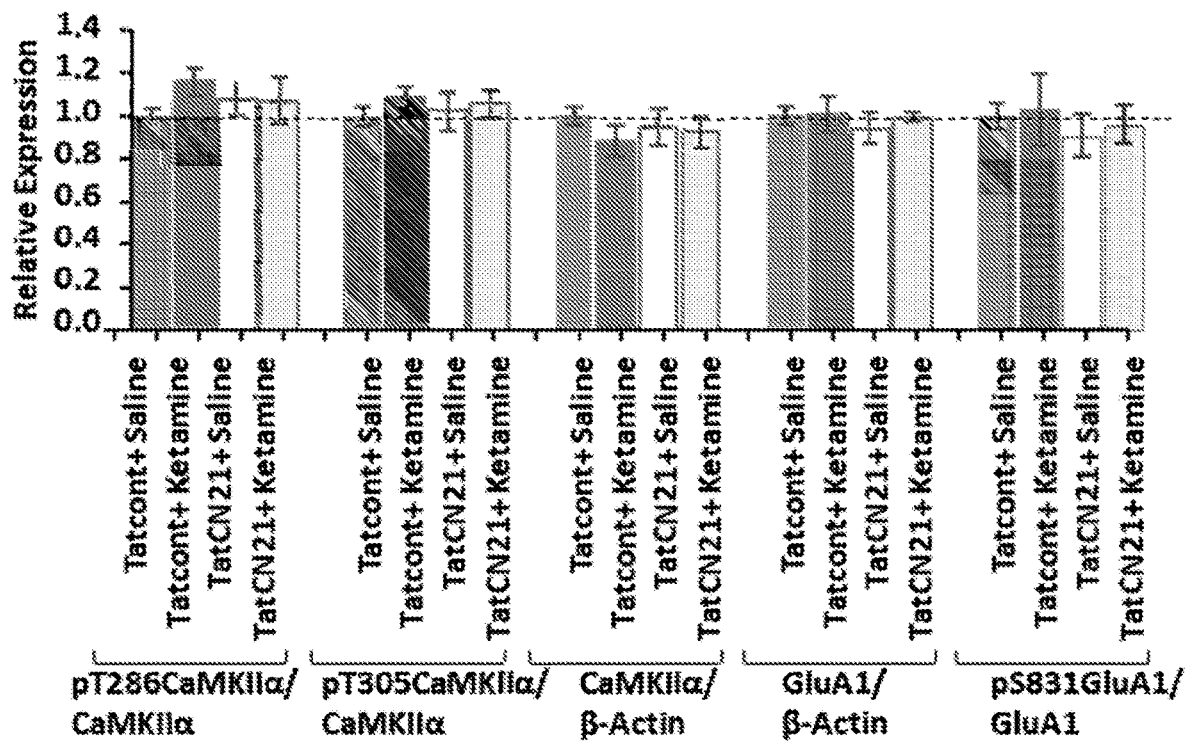
Figure 3K:
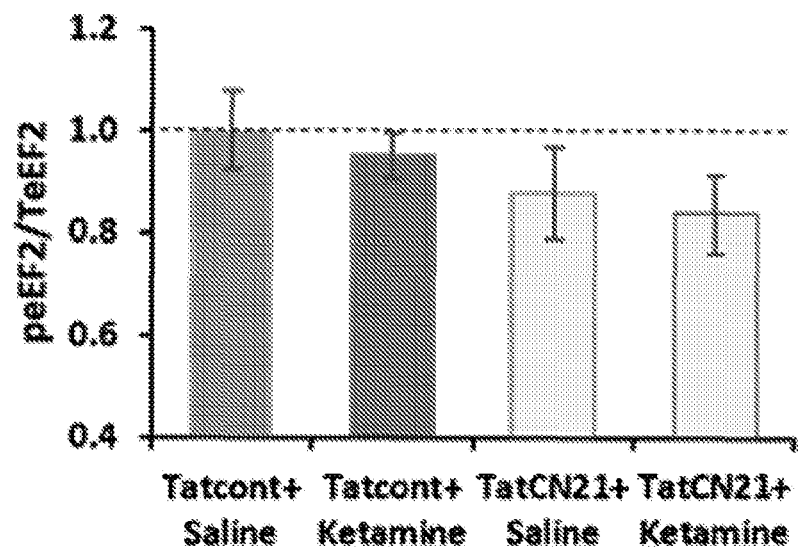
Figure 3L:
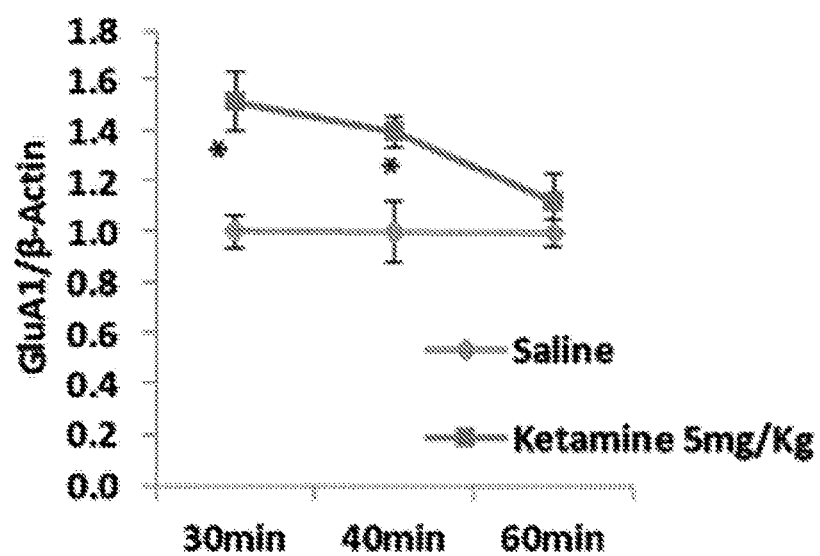

Next the possibility that ketamine administration dependent GluA1 induction is mediated via CaMKII signaling was tested. Ketamine administration dependent GluA1 induction in the hippocampal synaptosomes has been shown previously. Increased GluA1 insertion and expression in the synaptic membrane enhances the AMPA receptor calcium conductance and functions. TatCN21 (5 mg/kg b.w., i.p.) was injected 10 minutes before ketamine administration, and 3 hours later hippocampal tissue was excised. Using immunoblotting, it was found that CaMKIIa showed a trend towards higher phosphorylation of pT286, and there was no significant difference in any other protein examined, or their phosphorylation status (FIG. 3I-3K), suggesting that ketamine administration-dependent alteration in the function of CaMKII may persist for a few hours. While there is no significant difference in GluA1 expression 3 hours after the ketamine injection, increased expression levels of GluA1 was observed 20 and 40 minutes after ketamine administration in the C57BL/6 mice (FIG. 3L), indicating the possibility of biphasic induction of GluA1 following a low dose of ketamine in mice.

Figure 3M:
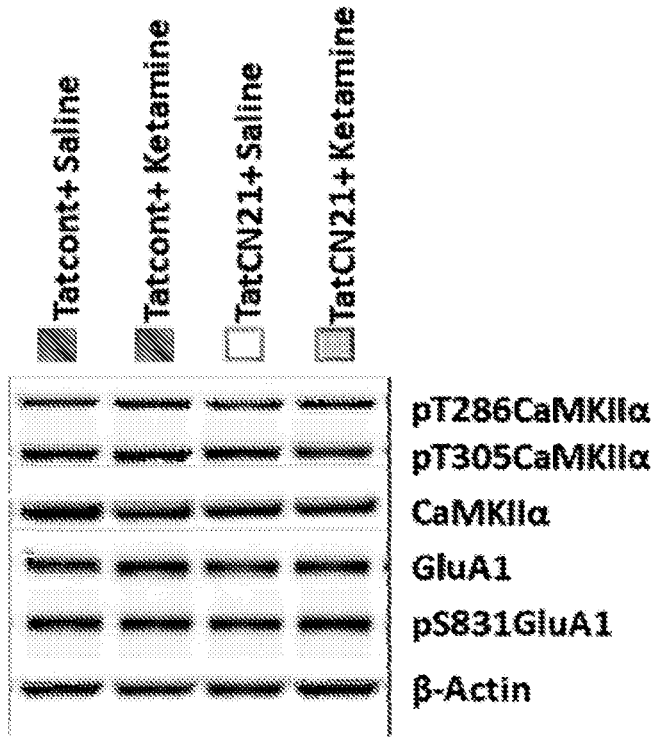
Figure 3N:
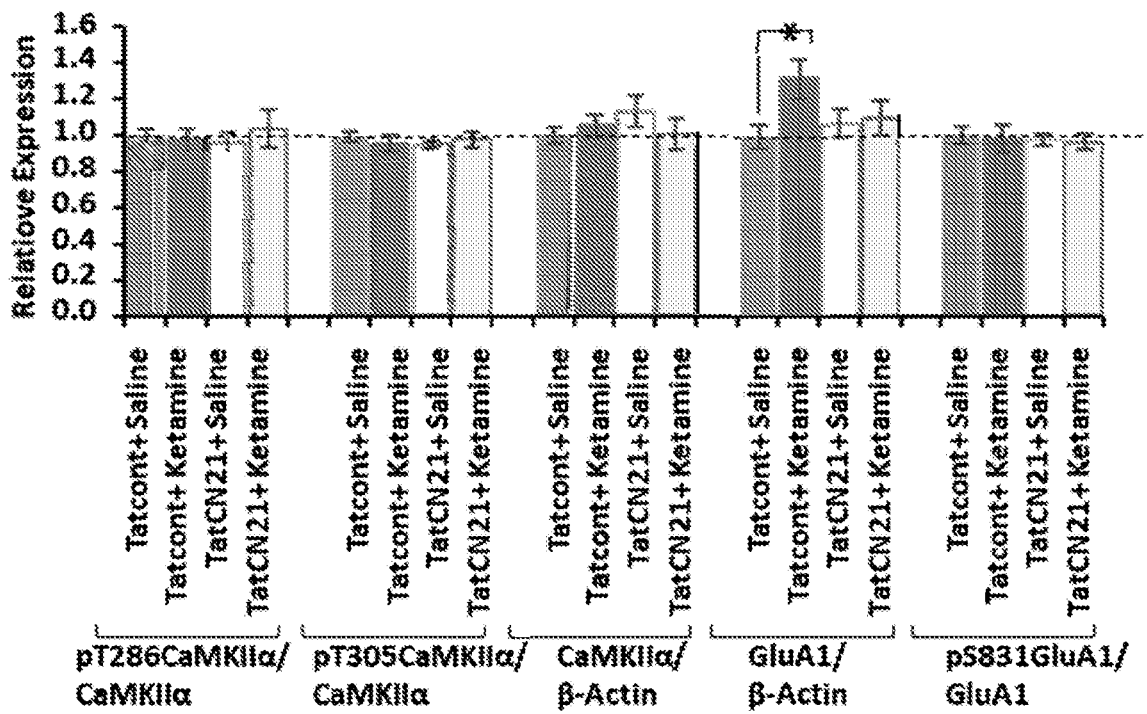

Next, the hippocampus was collected 24 hours following ketamine administration (FIG. 3M), and it was observed that GluA1 was markedly higher in the ketamine-injected group, but this induction of GluA1 was precluded in the TatCN21 injected group (FIG. 3M-3N).

Example 4

Figure 4A:
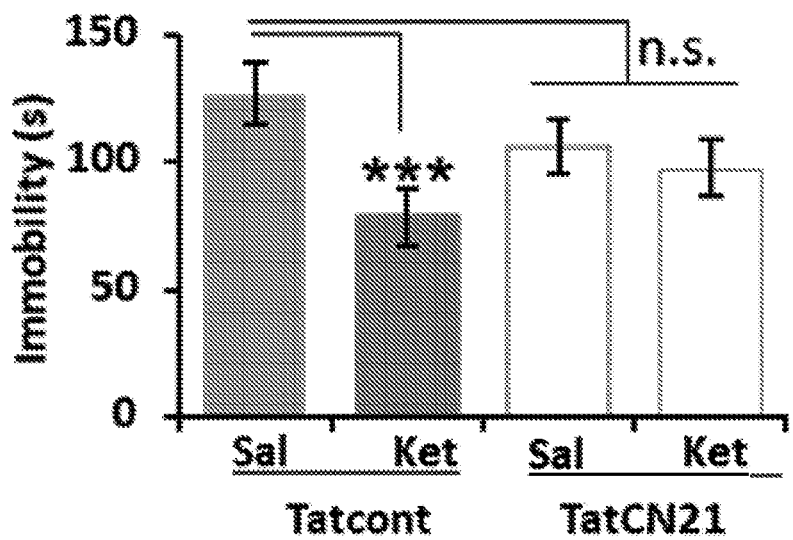
FIGS. 4A-4I. Systemic inhibition of CaMKII increases protein synthesis and prevents anti-depressant action of ketamine. (4A) Bar chart of immobility of mice in FST. (4B) Bar charts of the total velocity during the full 6 minutes of the FST. (4C) (Left) Representative immunoblots of hippocampus after SUnSET assay. (Right) Bar charts quantifying the global protein levels. (4D) Bar chart of immobility in FST 24 hours after administration of 5 or 10 mg/kg b.w. ketamine (4E) (Left) Representative immunoblots of hippocampus and cortex 24 hours after injection with saline or ketamine. (Right) Bar charts quantifying the GluA1 protein levels. (4F) Bar chart of the immobility time during FST 24 hours after injection of saline or ketamine in eEF2K-KO mice. (4G-4I) Bar chart quantification of the results of the (4G) FST, (4H) TST and (4I) the novelty suppressed feeding test.
Figure 4B:
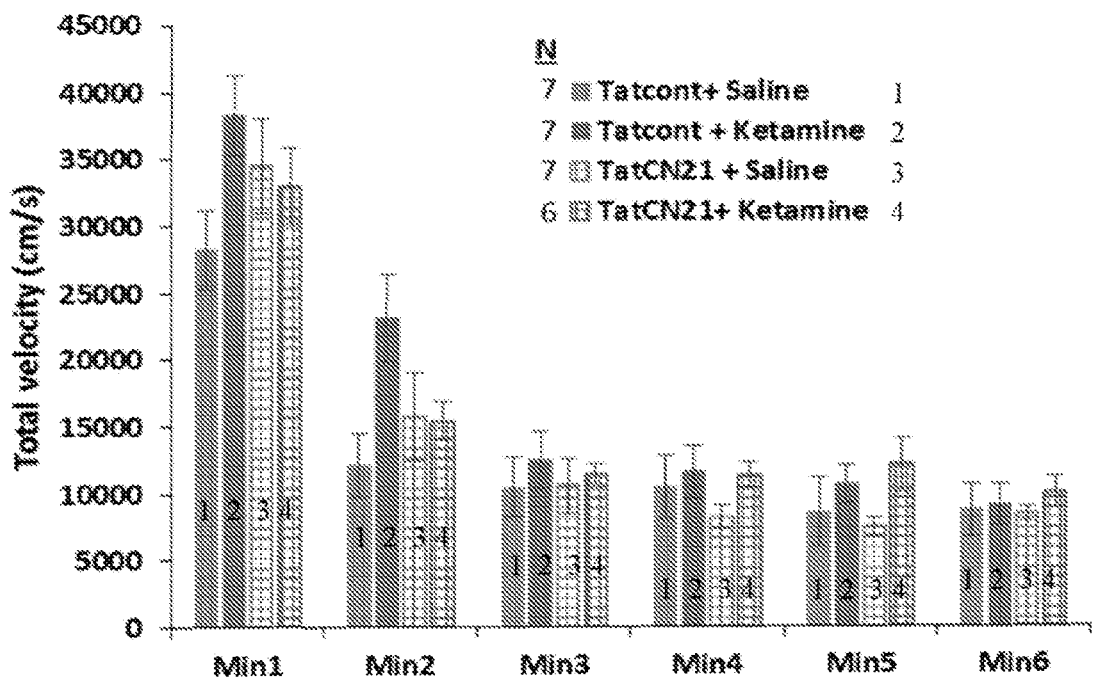

CaMKII Controls Ketamine-Mediated Anti-Depressant Effects and Global Protein Synthesis Given that ketamine administration leads to rapid regulation of CaMKII and eEF2K, the question of whether the anti-depressant behavioral effects of ketamine administration can be altered by CaMKII inhibition in an unavoidable depressive situation was examined next. C57BL/6 mice were injected intraperitoneally with the CaMKII inhibitor TatCN21 or Tatcont (control) 10 minutes before ketamine injection and were then subjected to the forced swim test (FIG. 4A). Ketamine injection led to shorter immobility time in the forced swim test in C57BL/6 mice. However, injection of CaMKII inhibitor 10 minutes before ketamine administration prevented this effect (FIG. 4A), indicating the indispensable role that CaMKII plays in eliciting the anti-depressant action of ketamine. While there is a trend towards increased swimming velocity in the Tatcont+ketamine injected group of mice during the first two minutes, no major significant difference between the groups was found, suggesting that the difference in immobile state cannot be attributed to changes in swimming speed in the FST (FIG. 4B).

Figure 4C:
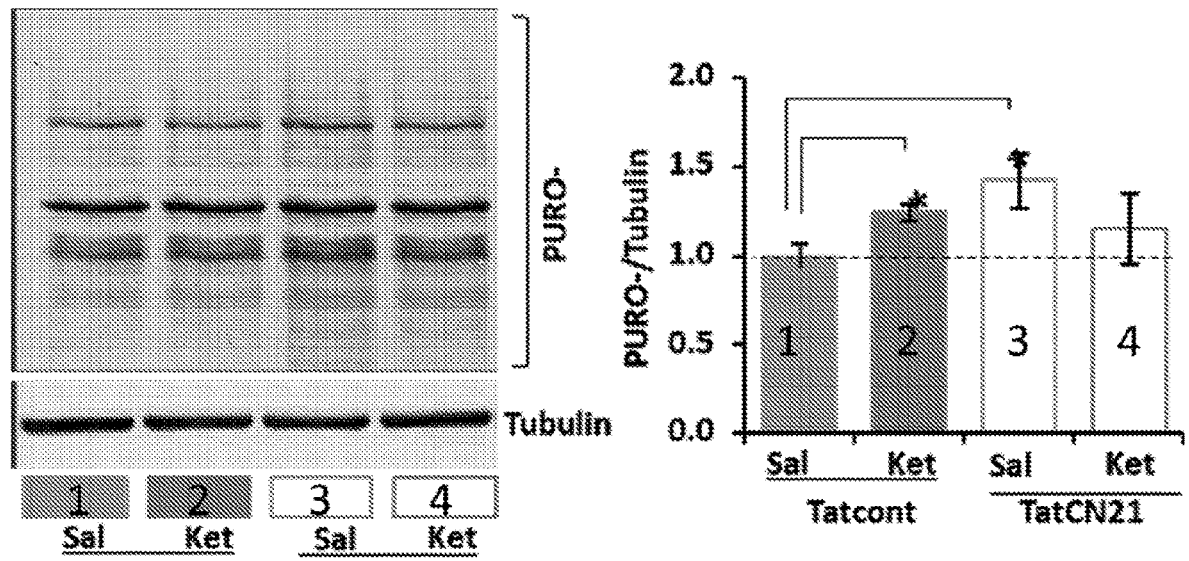

TatCN21-mediated occlusion of the effect of ketamine on FST behavior appears to be very similar to the phenocopying observed in eEF2K-KO mice. Thus, the effect of TatCN21 on ketamine mediated increased protein synthesis was further analyzed (FIG. 4C). Intriguingly, in a similar way to ketamine treatment i.p. injection of CaMKII inhibitor TatCN21 also increased protein synthesis in the hippocampus (FIG. 4C). Remarkably, similarly to the results observed in eEF2K-KO, TatCN21 partially prevented the increase in protein synthesis following ketamine administration. Together, these results suggest that shortly (about 20-30 minutes) after administration, ketamine affects both eEF2K and CaMKII to increase global protein synthesis (FIG. 4C).

Figure 4D:
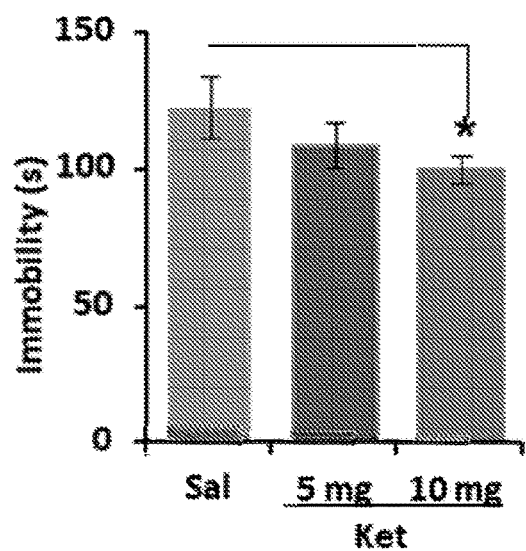
Figure 4E:
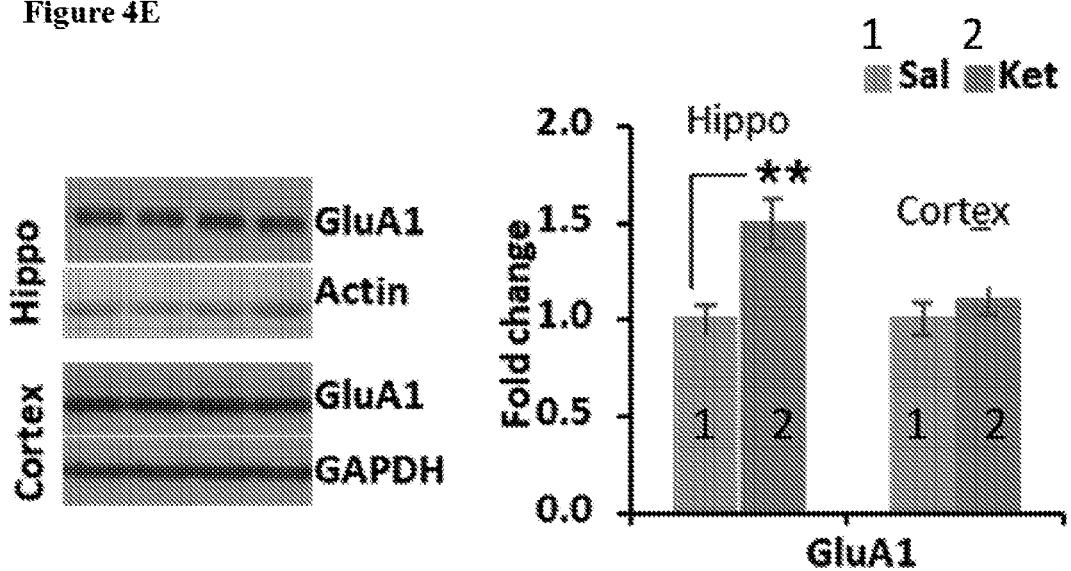

Single or repeated infusions of ketamine in humans result in acute dissociative and psychotomimetic effects, usually lasting for a few minutes to hours. Therefore, to investigate whether the long-term anti-depressant effect of ketamine (24 hours following injection) is also mediated by CaMKII and eEF2K, first a pilot experiment was conducted, where C57BL/6 mice were injected with 5 or 10 mg/kg b.w. ketamine and an FST was conducted 24 hours later. While both these concentration lead to shorter immobility time in FST, the group of mice that received 10 mg/kg exhibited less variability (FIG. 4D), and therefore, this concentration was chosen for subsequent experiments. Biochemically, both 5 and 10 mg/kg b.w. ketamine also induced GluA1 expression in the hippocampus (FIGS. 4B and 4E).

Figure 4F:
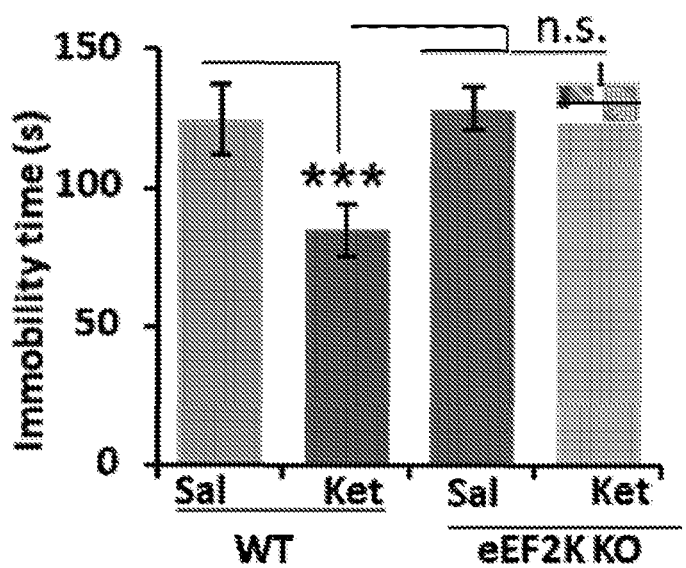

The behavioral experiments described thus far were performed within the time frame of up to 40 min following ketamine administration. Next, the long-term effects of ketamine were examined. For this purpose, FST was conducted in eEF2K-KO mice (FIG. 4F). Ketamine injection reduced immobility time in WT mice, however, eEF2K-KO mice showed no difference between the saline- and ketamine-injected groups in the FST test when performed 24 hours after the injection, indicating that the deletion of eEF2K makes the mice resistant to both short-term and long-term anti-depressant effects of ketamine (FIG. 4F). Interestingly, eEF2-KO mice did not show antidepressant behavior in novelty suppressed feeding (NSF) as had previously been shown in the art.

Figure 4G:
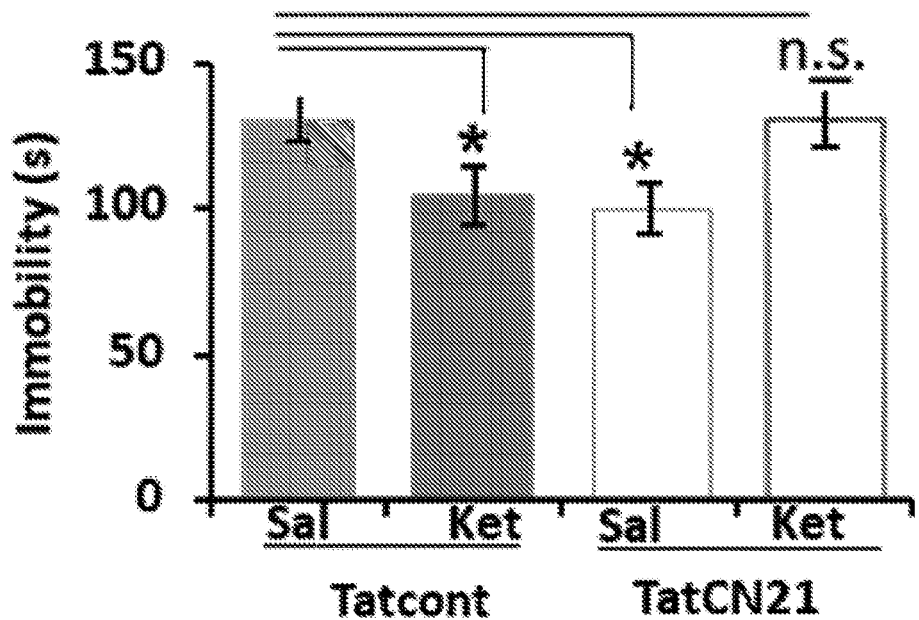
Figure 4H:
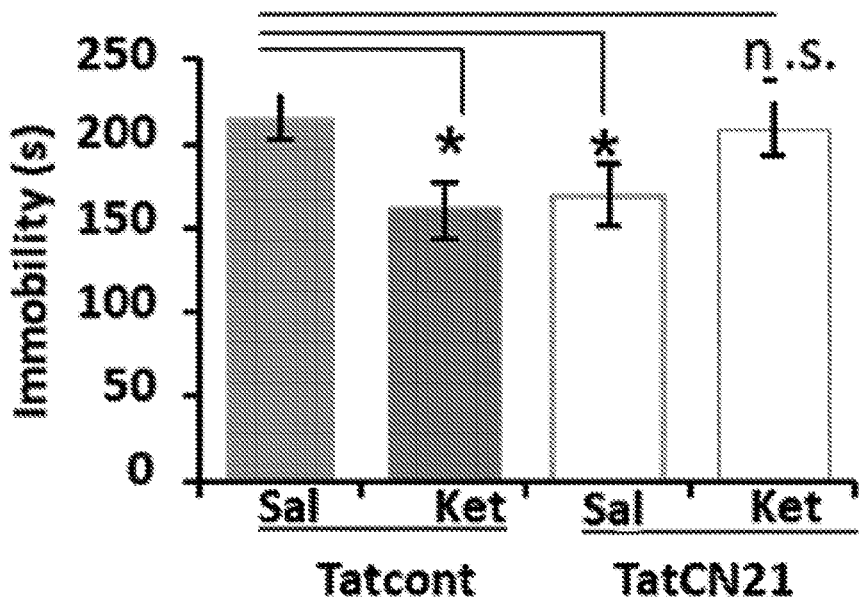
Figure 4I:
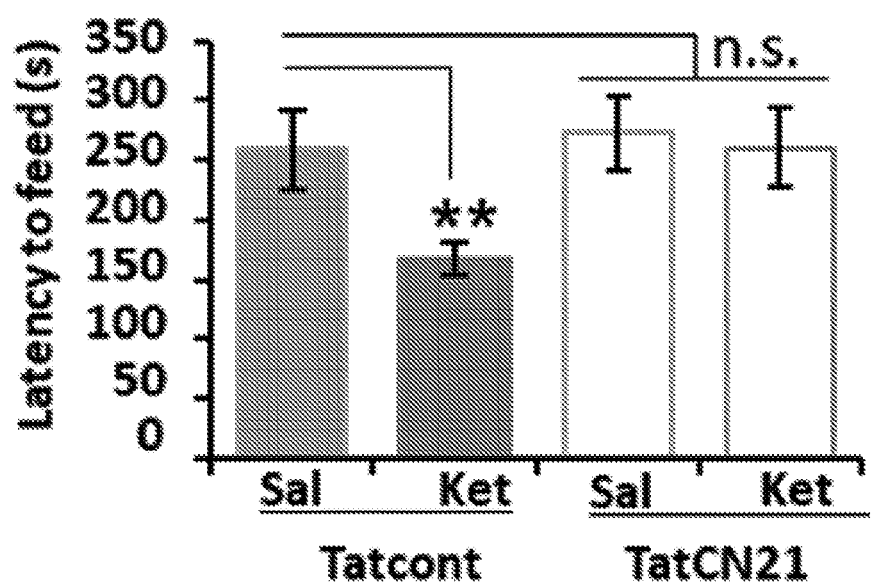

To examine the long term anti-depressant effects of ketamine that are mediated by CaMKII, C57BL/6 mice were injected with CaMKII inhibitor TatCN21 or Tatcont 10 minutes before injection of ketamine, and then subjected to the forced swim test or the tail suspension test (TST) 24 hours later (FIGS. 4G, and 4H respectively). Ketamine injection led to shorter immobility time in both the FST and the TST, whereas injection of the CaMKII inhibitor 10 min before administration of ketamine prevented this effect (FIG. 4G-4H). Moreover, injection of ketamine reduced the latency to feeding in the novelty suppressed feeding test. However, injection of TatCN21 prevented this effect, indicating that the decrease in latency to feed in response to ketamine administration is mediated by CaMKII (FIG. 4I). Together, these results suggest that CaMKII plays an indispensable role in eliciting the short- and long-term anti-depressant action of ketamine. It is important to note that in both the forced swim and the tail suspension tests the groups of mice that received a single injection of CaMKII inhibitor TatCN21 exhibited shorter immobility time (FIG. 4G-4H). However, such an anti-depressant response was not observed in the novelty suppressed feeding test (FIG. 4I). Together, these data extend the understanding of the mechanism underlying the anti-depressant actions of ketamine (FIG. 5).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for treating or ameliorating a depression, in a subject in need thereof, the method comprising administering to said subject a calcium/calmodulin-dependent protein kinase II (CaMKII) inhibitor, thereby treating depression, wherein said CaMKII inhibitor is TatCN21; wherein the method further comprising administering to said subject a CaMKII activator at least 30 minutes after administering said inhibitor.

2. The method of claim 1, wherein said depression is major depressive disorder.

3. The method of claim 1, wherein said CaMKII inhibitor inhibits calcium-stimulated substrate phosphorylation, autonomous substrate phosphorylation, or both.

4. The method of claim 1, wherein said CaMKII inhibitor increases auto-inhibitory phosphorylation of CaMKII.

5. The method of claim 4, wherein said inhibitory phosphorylation comprises phosphorylation of threonine 305 of CaMKIIalpha (CaMKIIa).

6. The method of claim 1, wherein said CaMKII inhibitor decreases auto-activating phosphorylation of CaMKII.

7. The method of claim 6, wherein said activating phosphorylation comprises phosphorylation of threonine 286 of CaMKIIa.

8. The method of claim 1, wherein said CaMKII inhibitor does not affect CaMKII protein levels.

9. The method of claim 1, wherein said subject is a human and between 0.08 mg/kg body weight (bw) and 0.8 mg/kg bw of said TatCN21 is administered.

10. The method of claim 9, wherein between 0.08 and 0.4 mg/kg bw is administered.

11. The method of claim 1, wherein said administering increases global protein synthesis in a brain tissue of the subject.

12. The method of claim 11, wherein said brain tissue is selected from hippocampus and cortex.

13. The method of claim 11, wherein said brain tissue is hippocampus.

14. The method of claim 1, wherein said treating or ameliorating occurs in less than 1 hour from said administering.

15. The method of claim 1, wherein said treating or ameliorating persists for at least 24 hours.

* * * * *

SEQUENCE LISTING

```
<160> NUMBER OF SEQ ID NOS: 4

<210> SEQ ID NO 1
<211> LENGTH: 21
<212> TYPE: PRT
<213> ORGANISM: Artificial
<220> FEATURE:
<223> OTHER INFORMATION: Synthetic

<400> SEQUENCE: 1

Lys Arg Pro Pro Lys Leu Gly Gln Ile Gly Arg Ser Lys Arg Val Val
1               5                   10                  15

Ile Glu Asp Asp Arg
            20

<210> SEQ ID NO 2
<211> LENGTH: 478
<212> TYPE: PRT
<213> ORGANISM: Homo sapiens

<400> SEQUENCE: 2

Met Ala Thr Ile Thr Cys Thr Arg Phe Thr Glu Glu Tyr Gln Leu Phe
1               5                   10                  15
```

Glu Glu Leu Gly Lys Gly Ala Phe Ser Val Val Arg Arg Cys Val Lys
            20                  25                  30

Val Leu Ala Gly Gln Glu Tyr Ala Ala Lys Ile Ile Asn Thr Lys Lys
        35                  40                  45

Leu Ser Ala Arg Asp His Gln Lys Leu Glu Arg Glu Ala Arg Ile Cys
 50                  55                  60

Arg Leu Leu Lys His Pro Asn Ile Val Arg Leu His Asp Ser Ile Ser
65                  70                  75                  80

Glu Glu Gly His His Tyr Leu Ile Phe Asp Leu Val Thr Gly Gly Glu
                85                  90                  95

Leu Phe Glu Asp Ile Val Ala Arg Glu Tyr Tyr Ser Glu Ala Asp Ala
        100                 105                 110

Ser His Cys Ile Gln Gln Ile Leu Glu Ala Val Leu His Cys His Gln
    115                 120                 125

Met Gly Val Val His Arg Asp Leu Lys Pro Glu Asn Leu Leu Leu Ala
    130                 135                 140

Ser Lys Leu Lys Gly Ala Ala Val Lys Leu Ala Asp Phe Gly Leu Ala
145                 150                 155                 160

Ile Glu Val Glu Gly Glu Gln Gln Ala Trp Phe Gly Phe Ala Gly Thr
                165                 170                 175

Pro Gly Tyr Leu Ser Pro Glu Val Leu Arg Lys Asp Pro Tyr Gly Lys
        180                 185                 190

Pro Val Asp Leu Trp Ala Cys Gly Val Ile Leu Tyr Ile Leu Leu Val
        195                 200                 205

Gly Tyr Pro Pro Phe Trp Asp Glu Asp Gln His Arg Leu Tyr Gln Gln
210                 215                 220

Ile Lys Ala Gly Ala Tyr Asp Phe Pro Ser Pro Glu Trp Asp Thr Val
225                 230                 235                 240

Thr Pro Glu Ala Lys Asp Leu Ile Asn Lys Met Leu Thr Ile Asn Pro
                245                 250                 255

Ser Lys Arg Ile Thr Ala Ala Glu Ala Leu Lys His Pro Trp Ile Ser
        260                 265                 270

His Arg Ser Thr Val Ala Ser Cys Met His Arg Gln Glu Thr Val Asp
    275                 280                 285

Cys Leu Lys Lys Phe Asn Ala Arg Arg Lys Leu Lys Gly Ala Ile Leu
    290                 295                 300

Thr Thr Met Leu Ala Thr Arg Asn Phe Ser Gly Gly Lys Ser Gly Gly
305                 310                 315                 320

Asn Lys Lys Ser Asp Gly Val Lys Glu Ser Ser Glu Ser Thr Asn Thr
                325                 330                 335

Thr Ile Glu Asp Glu Asp Thr Lys Val Arg Lys Gln Glu Ile Ile Lys
        340                 345                 350

Val Thr Glu Gln Leu Ile Glu Ala Ile Ser Asn Gly Asp Phe Glu Ser
    355                 360                 365

Tyr Thr Lys Met Cys Asp Pro Gly Met Thr Ala Phe Glu Pro Glu Ala
    370                 375                 380

Leu Gly Asn Leu Val Glu Gly Leu Asp Phe His Arg Phe Tyr Phe Glu
385                 390                 395                 400

Asn Leu Trp Ser Arg Asn Ser Lys Pro Val His Thr Thr Ile Leu Asn
                405                 410                 415

Pro His Ile His Leu Met Gly Asp Glu Ser Ala Cys Ile Ala Tyr Ile
        420                 425                 430

Arg Ile Thr Gln Tyr Leu Asp Ala Gly Gly Ile Pro Arg Thr Ala Gln

```
                  435                 440                 445
    Ser Glu Glu Thr Arg Val Trp His Arg Arg Asp Gly Lys Trp Gln Ile
                  450                 455                 460

Val His Phe His Arg Ser Gly Ala Pro Ser Val Leu Pro His
    465                 470                 475

<210> SEQ ID NO 3
<211> LENGTH: 542
<212> TYPE: PRT
<213> ORGANISM: Homo sapiens

<400> SEQUENCE: 3

Met Ala Thr Thr Val Thr Cys Thr Arg Phe Thr Asp Glu Tyr Gln Leu
1               5                   10                  15

Tyr Glu Asp Ile Gly Lys Gly Ala Phe Ser Val Val Arg Arg Cys Val
            20                  25                  30

Lys Leu Cys Thr Gly His Glu Tyr Ala Ala Lys Ile Ile Asn Thr Lys
        35                  40                  45

Lys Leu Ser Ala Arg Asp His Gln Lys Leu Glu Arg Glu Ala Arg Ile
    50                  55                  60

Cys Arg Leu Leu Lys His Ser Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
            100                 105                 110

Ala Ser His Cys Ile Gln Gln Ile Leu Glu Ala Val Leu His Cys His
        115                 120                 125

Gln Met Gly Val Val His Arg Asp Leu Lys Pro Glu Asn Leu Leu Leu
    130                 135                 140

Ala Ser Lys Cys Lys Gly Ala Ala Val Lys Leu Ala Asp Phe Gly Leu
145                 150                 155                 160

Ala Ile Glu Val Gln Gly Asp Gln Gln Ala Trp Phe Gly Phe Ala Gly
                165                 170                 175

Thr Pro Gly Tyr Leu Ser Pro Glu Val Leu Arg Lys Glu Ala Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala His Glu Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Lys Lys Phe Asn Ala Arg Arg Lys Leu Lys Gly Ala Ile
    290                 295                 300

Leu Thr Thr Met Leu Ala Thr Arg Asn Phe Ser Val Gly Arg Gln Thr
305                 310                 315                 320

Thr Ala Pro Ala Thr Met Ser Thr Ala Ala Ser Gly Thr Thr Met Gly
                325                 330                 335
```

```
Leu Val Glu Gln Ala Lys Ser Leu Leu Asn Lys Lys Ala Asp Gly Val
            340                 345                 350

Lys Pro Gln Thr Asn Ser Thr Lys Asn Ser Ala Ala Ala Thr Ser Pro
            355                 360                 365

Lys Gly Thr Leu Pro Pro Ala Ala Leu Glu Pro Gln Thr Thr Val Ile
            370                 375                 380

His Asn Pro Val Asp Gly Ile Lys Glu Ser Ser Asp Ser Ala Asn Thr
385                         390                 395                 400

Thr Ile Glu Asp Glu Asp Ala Lys Ala Arg Lys Gln Glu Ile Ile Lys
                405                 410                 415

Thr Thr Glu Gln Leu Ile Glu Ala Val Asn Asn Gly Asp Phe Glu Ala
                420                 425                 430

Tyr Ala Lys Ile Cys Asp Pro Gly Leu Thr Ser Phe Glu Pro Glu Ala
            435                 440                 445

Leu Gly Asn Leu Val Glu Gly Met Asp Phe His Arg Phe Tyr Phe Glu
            450                 455                 460

Asn Leu Leu Ala Lys Asn Ser Lys Pro Ile His Thr Thr Ile Leu Asn
465                 470                 475                 480

Pro His Val His Val Ile Gly Glu Asp Ala Ala Cys Ile Ala Tyr Ile
                485                 490                 495

Arg Leu Thr Gln Tyr Ile Asp Gly Gln Gly Arg Pro Arg Thr Ser Gln
            500                 505                 510

Ser Glu Glu Thr Arg Val Trp His Arg Arg Asp Gly Lys Trp Gln Asn
            515                 520                 525

Val His Phe His Cys Ser Gly Ala Pro Val Ala Pro Leu Gln
530                 535                 540

<210> SEQ ID NO 4
<211> LENGTH: 12
<212> TYPE: PRT
<213> ORGANISM: Human immunodeficiency virus

<400> SEQUENCE: 4

Gly Arg Lys Lys Arg Arg Gln Arg Arg Arg Pro Gln
1               5                   10
```